(12) United States Patent
Belgorod

(10) Patent No.: US 7,759,317 B2
(45) Date of Patent: Jul. 20, 2010

(54) ANALGESIC AND ANTI-INFLAMMATORY COMPOSITIONS AND METHODS WITH FLAVONOID GLYCOSIDE-TYPE COMPOUNDS

(75) Inventor: Barry Miles Belgorod, New York, NY (US)

(73) Assignee: BMB Patent Holding Corporation, New York, NY (US)

( * ) Notice: Subject to any disclaimer, the term of this patent is extended or adjusted under 35 U.S.C. 154(b) by 390 days.

(21) Appl. No.: 11/966,795

(22) Filed: Dec. 28, 2007

(65) Prior Publication Data

US 2008/0171708 A1    Jul. 17, 2008

Related U.S. Application Data

(60) Provisional application No. 60/882,278, filed on Dec. 28, 2006.

(51) Int. Cl.
*A01N 43/04* (2006.01)
*A61K 31/70* (2006.01)

(52) U.S. Cl. ............... 514/35; 514/25; 514/27
(58) Field of Classification Search ............ None
See application file for complete search history.

(56) References Cited

OTHER PUBLICATIONS

Lu et al. Clinica Chimica Acta (2002), vol. 316, pp. 95-99.*
Yoon et al. Arch. Pharm. Res. (2004), vol. 27, pp. 454-459.*

* cited by examiner

*Primary Examiner*—Patrick T Lewis
(74) *Attorney, Agent, or Firm*—Keith R. Lange

(57) ABSTRACT

The present invention relates to pharmaceutical compositions containing certain flavonoid glycoside-type compounds that have been shown in the present invention to be therapeutically useful, including useful as analgesics and anti-inflammatories for the treatment and management of pain and inflammatory conditions. Methods for the therapeutic uses of such compounds and pharmaceutical compositions is also provided.

11 Claims, 8 Drawing Sheets

Formula IV

Formula XXVII

Formula XIII

Formula XXXIII

Formula XIX

Formula XXXVII

Formula X

Chemical Formula: $C_{26}H_{28}O_{15}$
Molecular Weight: 580.49

Formula $X_1$

ANALGESIC AND ANTI-INFLAMMATORY COMPOSITIONS AND METHODS WITH FLAVONOID GLYCOSIDE-TYPE COMPOUNDS

RELATED APPLICATION DATA

This application claims priority to U.S. Provisional Patent Application No. 60/882,278, filed on Dec. 28, 2006, the entirety of which is hereby incorporated by reference.

FIELD OF THE INVENTION

The present invention relates to pharmaceutical compositions containing certain flavonoid glycoside-type compounds that have been shown in the present invention to be therapeutically useful, and in particular have been shown to be useful as analgesics and anti-inflammatory for the treatment and management of pain and inflammatory conditions; and further relates to the therapeutic use of such pharmaceutical compositions and compounds in the treatment and management of pain and inflammatory conditions, and other disorders in patients. The compounds may be synthesized or they may be isolated from the fruit of the genus *Capsicum*, in particular *Capsicum annuum*.

BACKGROUND OF RELATED TECHNOLOGY

A primary focus of drug research is the development of analgesics for pain management. Analgesics render sensory pathways insensible or less sensible to pain, whereas anesthetics act on all sensory pathways rendering them insensible to pain, temperature, touch, proprioception and skeletal muscle tone. As such, although anesthetics can be used for pain management, their utility is limited by their inhibition of these other sensory pathways. For example, it may be desired to control a patient's pain associated with an oral mucosal lesion without interfering with senses of touch, proprioception (to avoid biting of the tongue) or taste (so as not to interfere with appetite), which is not generally possible with topical anesthetics (for example, Benzocaine) which are not able to selectively inhibit pain. The use of analgesics to control pain in such circumstances is therefore desirable.

Analgesics are generally classified as either narcotic (opioids) or non-narcotic. Narcotic analgesics primarily act on the central nervous system and carry potentially life-threatening side-effects such as addiction, impaired higher cortical function and depressed respiration. As a result, their use is regulated and they may only be prescribed by licensed practitioners. Non-narcotic analgesics include salicylates, such as aspirin; acetaminophen; and non-steroidal anti-inflammatory drugs ("NSAIDS"), such as cyclooxygenase-2 ("Cox-2") inhibitors. Such non-narcotic analgesics can be limited in their ability to control pain and may have the side effects of chemical irritation, anticoagulation, myocardial infarction and stroke. Accordingly, there is a continuing need for the discovery and development of new analgesics, and in particular non-narcotic analgesics, that are useful for the localized management of pain without an undesirable side effects profile.

In this regard, various plant-derived compounds have been investigated for their analgesic properties. For example, capsaicin, a vanillyl alkaloid that is the source of pungency in hot peppers, has been used to treat the pain of arthritis, osteoarthritis, and various peripheral neuropathies. See, for example, Cordell and Araujo, *The Annals of Pharmacotherapy*, (1993) 27:330; Levinson, (January/February 1995) *The Sciences*, pp. 13-15. However, the therapeutic usefulness of capsaicin is limited due to an adverse side effects profile that includes burning sensations and erythema, and such side effects may persist over time. By way of further example, extracts of sweet bell peppers (*Capsicum annuum*) have been shown to exhibit analgesic properties (see, for example, U.S. Pat. Nos. 6,060,060 and 6,086,888), but the specific compound(s) responsible for such analgesic effects have not been identified. Furthermore, as such extracts must be derived from naturally-occurring fruit, their production and practical use is limited.

Moreover, certain naturally-occurring flavonoid glycosides have been reported, including luteolin 7-(6″-β-D-apiofuranosyl)-β-D-glucopyranoside, alternatively named: 7-[(6-O-D*-apio-beta-D*-furanosyl-beta-D*-glucopyranosyl)oxy]-2-(3,4-dihydroxyphenyl)-5-hydroxy-4H-1-benzopyran-4-one (Bucar, F. et al. *Phytochemistry* (1998), 48 573-575), but have not been shown to be therapeutically useful.

SUMMARY OF THE INVENTION

The present invention is directed to the discovery that certain flavonoid glycoside compounds are useful as therapeutic agents for a variety of therapeutic uses; and in particular as analgesics and anti-inflammatories for the prevention, treatment and management of pain and inflammatory conditions. As described herein, such compounds have been isolated, purified, identified, and shown to have therapeutic utility. The identification and characterization of these compounds, pharmaceutical compositions including such compounds, and methods of making and using such compounds and pharmaceutical compositions of the present invention, are the result of research efforts described herein that stem from the unexpected discovery that the puree or juice of sweet peppers exhibits an analgesic effect on inflamed pharyngeal mucosa, without the burning sensation or pungency that accompanies the use of capsaicin or the purees or juices of peppers exhibiting pungency. The embodiments of the present invention discussed herein are intended, and are to be taken, to illustrate various aspects of the present invention and provide certain teachings to those of skill in the relevant art, and in no way limit the scope of the present invention.

In this regard, in certain example (non-limiting) embodiments, the present invention is directed to pharmaceutical compositions, comprising a therapeutically effective amount of a compound according to Formula IV:

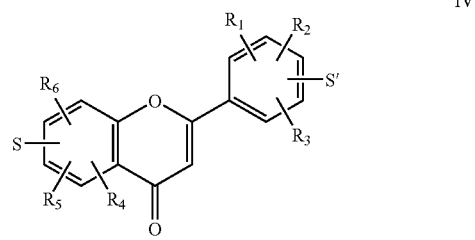

or a pharmaceutically-acceptable salt, enantiomer, diasteriomer, racemic mixture, enantiomerically-enriched mixture, solvate, or prodrug of a compound according to Formula IV, in a pharmaceutically effective carrier; and which is present in an analgesically-effective amount, wherein each of $R_1$, $R_2$, $R_3$, $R_4$, $R_5$ and $R_6$ is independently H, OH, OCH$_3$, or a substituted or unsubstituted: alkyl; alkenyl; or alkynyl group; wherein each of $R_1$, $R_2$, $R_3$, $R_4$, $R_5$ and $R_6$ may be substituted at any unsubstituted position on its respective ring structure; wherein each of S and S' is independently a carbohydrate moiety; wherein at least one of S and S' is present, and the other of S and S' is optionally present; and wherein, when present, each of S and S' is bound to its respective ring structure through one of $R_1$, $R_2$, $R_3$, $R_4$, $R_5$ or $R_6$. In the compounds discussed herein, S and S' may be independently selected from the group consisting of: a substituted or unsubstituted monosaccharide (for example and without limitation: glucose; fructose; galactose; rhamnose; xylose; or arabinose); a substituted or unsubstituted disaccharide (for example and without limitation: sucrose; maltose; or lactose); a substituted or unsubstituted trisaccharide; a substituted or unsubstituted oligosaccharide; and an apiofuranosyl-glucopyranosyl.

In any of the preceding or alternative embodiments, the present invention is directed to a pharmaceutical composition comprising a therapeutically effective amount of a compound of Formula Va

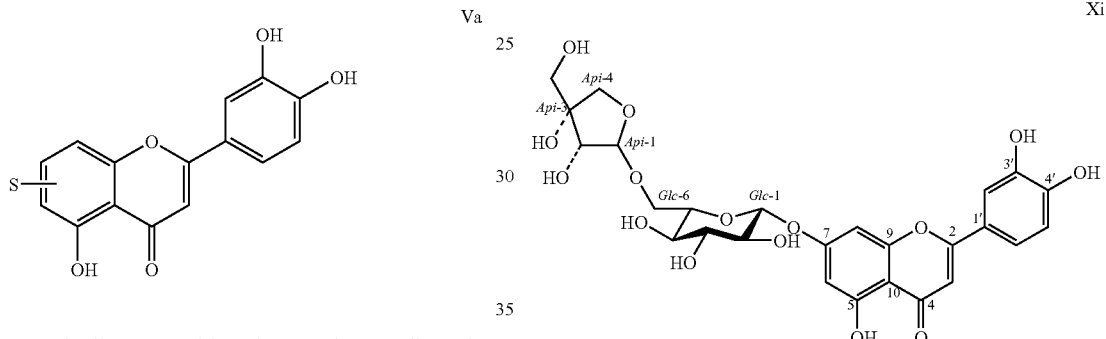

Va or a pharmaceutically-acceptable salt, enantiomer, diasteriomer, racemic mixture, enantiomerically-enriched mixture, solvate, or prodrug thereof, in a pharmaceutically effective carrier, wherein S is a carbohydrate moiety; and wherein the compound according to Formula Va is present in the pharmaceutical composition an amount that is therapeutically effective to effect analgesia in a mammal. In some embodiments, S may be selected from the group consisting of: a substituted or unsubstituted monosaccharide; a substituted or unsubstituted disaccharide; a substituted or unsubstituted trisaccharide; a substituted or unsubstituted oligosaccharide; and an apiofuranosyl-glucopyranosyl.

In any of the preceding or alternative embodiments, the compound according to Formula Va is a compound of Formula VIII

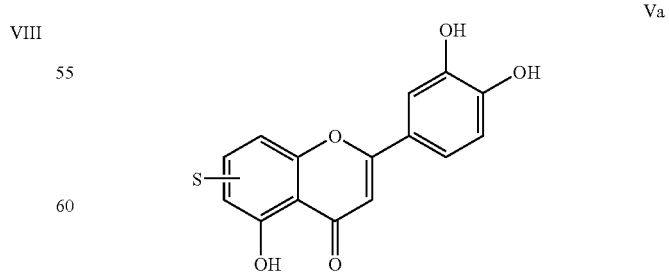

VIII wherein S is a carbohydrate moiety, and may be as defined herein.

In any of the preceding or alternative embodiments, the present invention is directed to a pharmaceutical composition comprising a therapeutically effective amount of a compound of Formula X

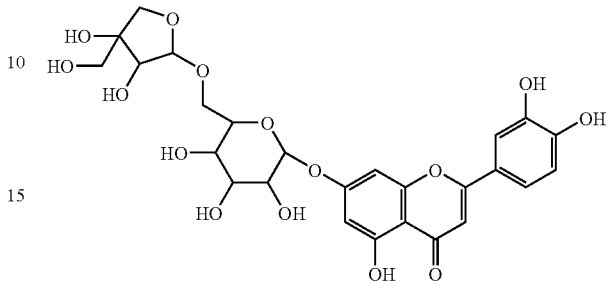

X or Formula Xi

Xi or a pharmaceutically-acceptable salt, enantiomer, diasteriomer, racemic mixture, enantiomerically-enriched mixture, solvate, or prodrug thereof, in a pharmaceutically effective carrier. In any of the preceding or alternative embodiments, the compound of Formula X or Xi is present in an amount that is therapeutically effective to effect analgesia or reduce inflammation in a mammal.

In any of the preceding or alternative embodiments, the present invention is directed to a method for effecting analgesia in a mammal, comprising administering to a mammal a pharmaceutical composition comprising a therapeutically effective amount of a compound of Formula Va Va or a pharmaceutically-acceptable salt, enantiomer, diasteriomer, racemic mixture, enantiomerically-enriched mixture, solvate, or prodrug thereof, in a pharmaceutically effective carrier, wherein S is a carbohydrate moiety; and wherein said compound according to Formula Va is present in said pharmaceutical composition an amount that is therapeutically effective to effect analgesia in a mammal.

In any of the preceding or alternative embodiments, the present invention is directed to a method for effecting analgesia in a mammal, wherein the compound according to Formula Va is a compound of Formula VIII

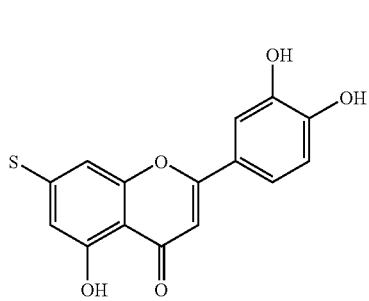

wherein S is a carbohydrate moiety, and may be as defined herein.

In any of the preceding or alternative embodiments, the present invention is directed to a method for providing therapeutic treatment to a mammal, comprising administering to a mammal a pharmaceutical composition comprising a therapeutically effective amount of a compound of Formula X

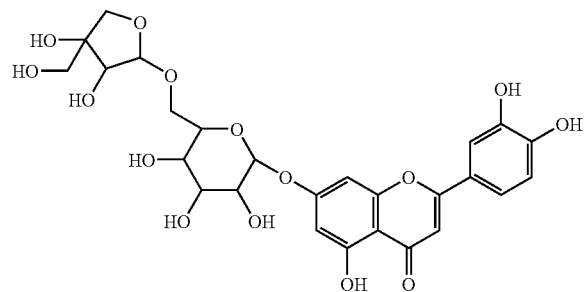

or Formula Xi

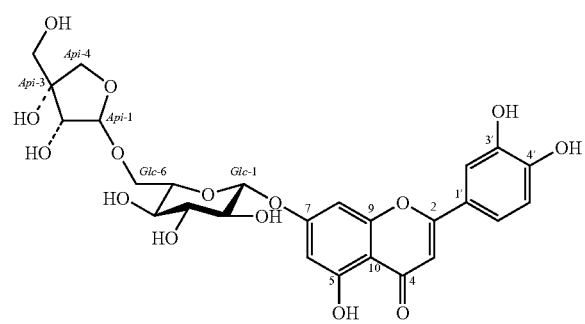

or a pharmaceutically-acceptable salt, enantiomer, diasteriomer, racemic mixture, enantiomerically-enriched mixture, solvate, or prodrug thereof, in a pharmaceutically effective carrier. In any of the preceding or alternative embodiments, the compound of Formula X or Xi may be present in said pharmaceutical composition in an amount that is therapeutically effective to effect analgesia or reduce inflammation in a mammal.

In any of the preceding or alternative embodiments, a compound according to Formula IV is a compound according to Formula V:

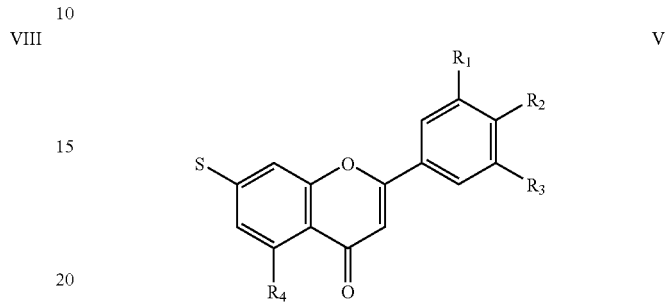

wherein each of $R_1$, $R_2$, $R_3$, and $R_4$ is independently H, OH, $OCH_3$, or a substituted or unsubstituted: alkyl; alkenyl; or alkynyl group; and wherein S is a carbohydrate moiety. In one embodiment, $R_1$ is H, $R_2$ is OH, $R_3$ is H, $R_4$ is OH; and S is a carbohydrate moiety; and in another embodiment $R_1$ is OH, $R_2$ is OH, $R_3$ is H, $R_4$ is OH; and S is a carbohydrate moiety.

In any of the preceding or alternative embodiments, a compound according to Formula V is a compound according to Formula IX:

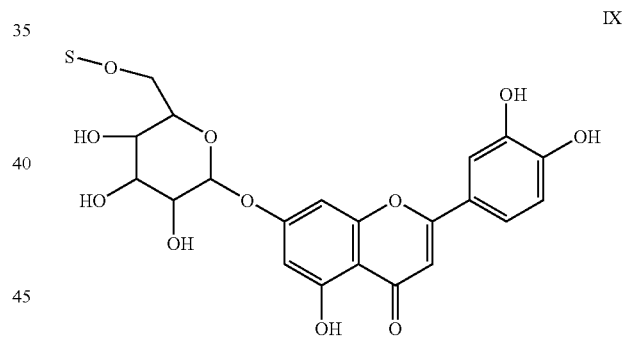

wherein S is a carbohydrate moiety; and in another embodiment the compound according to Formula V is a compound of Formula X:

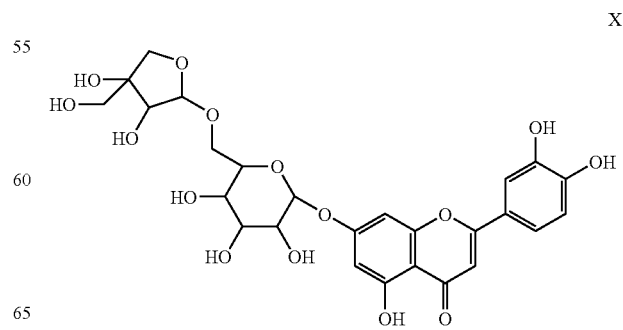

Pharmaceutical compositions used in any of the preceding or alternative embodiments of the present invention may include a compound in an analgesically effective amount between about 0.01 mg to about 500 mg per unit dose, and in particular between about 1 mg to about 100 mg per unit dose; and may be in the form of an immediate-release, controlled-release, or sustained-release orally-administrable composition (for example and without limitation, a pill, tablet, capsule, gelcap, lozenge, throat spray, solution, emulsion, cream, paste, gel, cough drop, dissolvable strip, lollipop, or gum); may be in the form of a topically-administrable composition (for example and without limitation, a liquid solution, liquid spray, emulsion, cream, paste, gel, lotion, foam, or impregnated dressing); may be in the form of an occularly-administrable composition (for example and without limitation, eyedrops); and may be administered to the sinuses, throat, or lungs (for example and without limitation, in the form of inhalable particles, inhalable solution, droplets, or aerosol).

In any of the preceding or alternative embodiments, a compound used in the present invention, or a pharmaceutically-acceptable salt, enantiomer, diasteriomer, racemic mixture, enantiomerically-enriched mixture, solvate, or prodrugs of a compound used in the present invention, is produced synthetically or semi-synthetically; and may be isolated and purified from a naturally occurring organism, which may be, for example and without limitation, a fruit of the genus *Capsicum*, for example *C. annuum*.

In any of the preceding or alternative embodiments, one or more various therapeutic agents may be used in combination with a compound used in the present invention, or a pharmaceutically-acceptable salt, enantiomer, diasteriomer, racemic mixture, enantiomerically-enriched mixture, solvate, or prodrug of a compound used in the present invention. Such therapeutic agents include for example and without limitation, analgesics, such as an NSAIDs (which may be selected from, for example and without limitation, salicylates, acetaminophen, ibuprofen and COX-2 inhibitors).

In any of the preceding or alternative embodiments, the present invention is directed to a pharmaceutical composition, comprising a therapeutically effective amount of a compound of Formula X

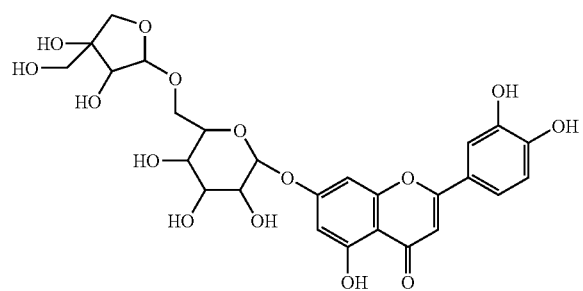

X or a pharmaceutically-acceptable salt, enantiomer, diasteriomer, racemic mixture, enantiomerically-enriched mixture, solvate, or prodrug of a compound of Formula X, in a pharmaceutically effective carrier.

In any of the preceding or alternative embodiments, the present invention is directed to a pharmaceutical composition, comprising a therapeutically effective amount of a compound according to Formula XIII:

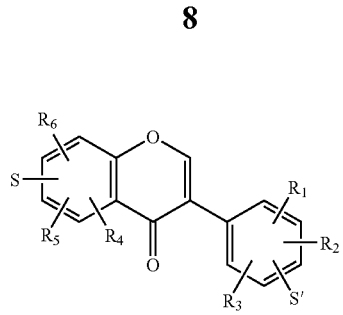

XIII or a pharmaceutically-acceptable salt, enantiomer, diasteriomer, racemic mixture, enantiomerically-enriched mixture, solvate, or prodrug of a compound according to Formula XIII, in a pharmaceutically effective carrier; and which is present in an analgesically-effective amount, wherein each of $R_1$, $R_2$, $R_3$, $R_4$, $R_5$ and $R_6$ is independently H, OH, $OCH_3$, or a substituted or unsubstituted: alkyl; alkenyl; or alkynyl group; wherein each of $R_1$, $R_2$, $R_3$, $R_4$, $R_5$ and $R_6$ may be substituted at any unsubstituted position on its respective ring structure; wherein each of S and S' is independently a carbohydrate moiety; wherein at least one of S and S' is present, and the other of S and S' is optionally present; and wherein, when present, each of S and S' is bound to its respective ring structure through one of $R_1$, $R_2$, $R_3$, $R_4$, $R_5$ or $R_6$.

In any of the preceding or alternative embodiments, a compound according to Formula XIII is a compound according to Formula XIV:

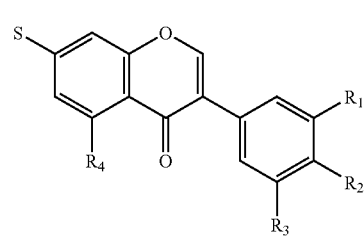

XIV wherein each of $R_1$, $R_2$, $R_3$, and $R_4$ is independently H, OH, $OCH_3$, or a substituted or unsubstituted: alkyl; alkenyl; or alkynyl group; and wherein S is a carbohydrate moiety.

In any of the preceding or alternative embodiments, a compound according to Formula XIII is a compound according to Formula XV:

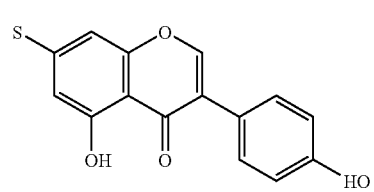

XV wherein S is a carbohydrate moiety.

In any of the preceding or alternative embodiments, a compound according to Formula XIII is a compound according of Formula XVI:

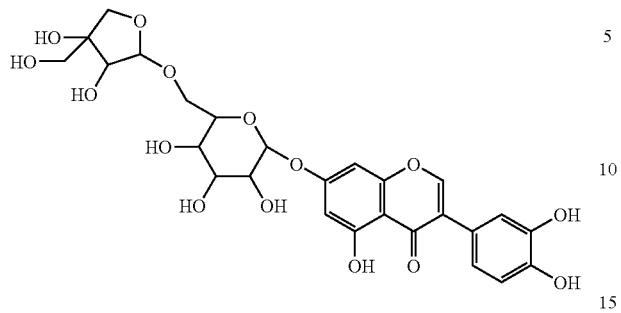

XVI

In any of the preceding or alternative embodiments, the present invention is directed to a pharmaceutical composition, comprising a therapeutically effective amount of a compound according to Formula XIX:

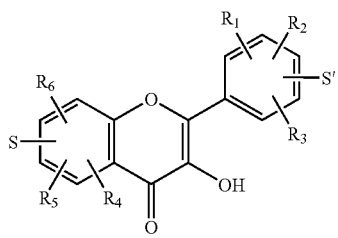

XIX or a pharmaceutically-acceptable salt, enantiomer, diasteriomer, racemic mixture, enantiomerically-enriched mixture, solvate, or prodrug of a compound according to Formula XIX, in a pharmaceutically effective carrier; and which is present in an analgesically-effective amount, wherein each of $R_1$, $R_2$, $R_3$, $R_4$, $R_5$ and $R_6$ is independently H, OH, OCH$_3$, or a substituted or unsubstituted: alkyl; alkenyl; or alkynyl group; wherein each of $R_1$, $R_2$, $R_3$, $R_4$, $R_5$ and $R_6$ may be substituted at any unsubstituted position on its respective ring structure; wherein each of S and S' is independently a carbohydrate moiety; wherein at least one of S and S' is present, and the other of S and S' is optionally present; and wherein, when present, each of S and S' is bound to its respective ring structure through one of $R_1$, $R_2$, $R_3$, $R_4$, $R_5$, $R_6$, or the indicated 3-OH group.

In any of the preceding or alternative embodiments, a compound according to Formula XIX is a compound according to Formula XX:

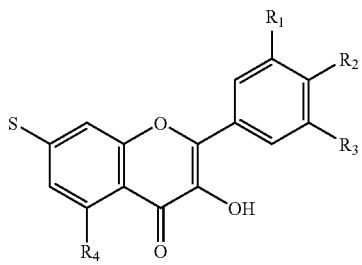

XX wherein each of $R_1$, $R_2$, $R_3$, and $R_4$ is independently H, OH, OCH$_3$, or a substituted or unsubstituted: alkyl; alkenyl; or alkynyl group; and wherein S is a carbohydrate moiety.

In any of the preceding or alternative embodiments, a compound according to Formula XIX is a compound according to Formula XXI:

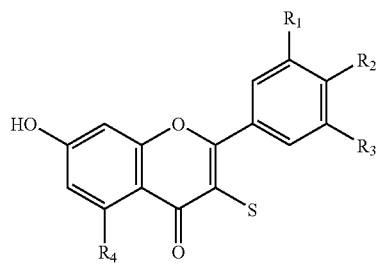

XXI wherein each of $R_1$, $R_2$, $R_3$, and $R_4$ is independently H, OH, OCH$_3$, or a substituted or unsubstituted: alkyl; alkenyl; or alkynyl group; and wherein S is a carbohydrate moiety.

In any of the preceding or alternative embodiments, a compound according to Formula XXI is a compound according to Formula XXII:

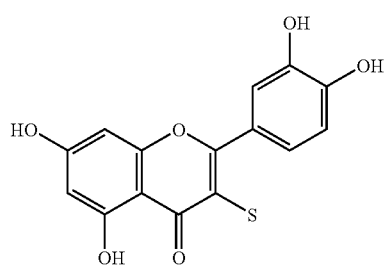

XXII wherein S is a carbohydrate moiety.

In any of the preceding or alternative embodiments, a compound according to Formula XIX is a compound of Formula XXIII:

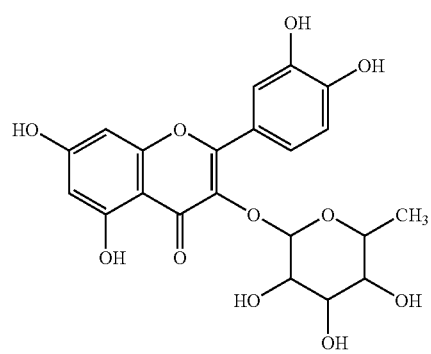

XXIII

In any of the preceding or alternative embodiments, a compound according to Formula XIX is a compound of Formula XXIV:

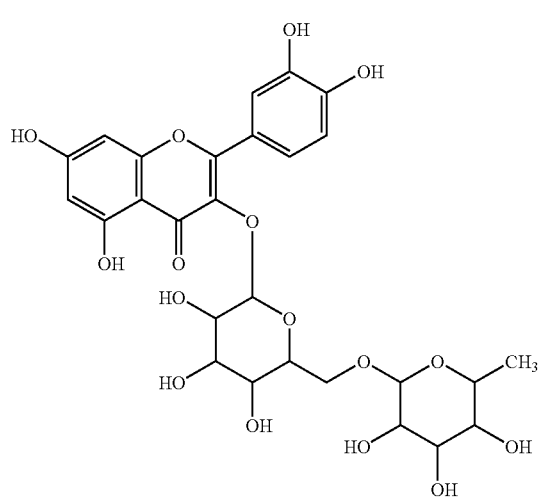

XXIV

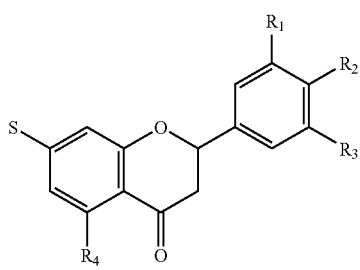

XXVIII wherein each of $R_1$, $R_2$, $R_3$, and $R_4$ is independently H, OH, $OCH_3$, or a substituted or unsubstituted: alkyl; alkenyl; or alkynyl group; and wherein S is a carbohydrate moiety.

In any of the preceding or alternative embodiments, a compound according to Formula XXVII is a compound of Formula XXIX:

In any of the preceding or alternative embodiments, the present invention is directed to a pharmaceutical composition, comprising a therapeutically effective amount of a compound according to Formula XXVII:

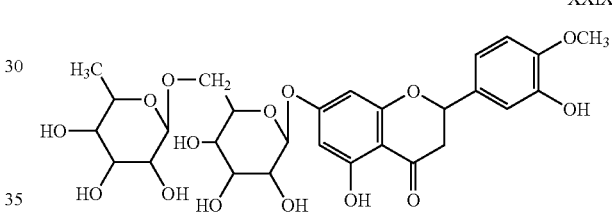

XXIX

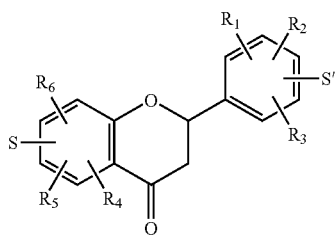

XXVII

In any of the preceding or alternative embodiments, a compound according to Formula XXVII is a compound of Formula XXX:

or a pharmaceutically-acceptable salt, enantiomer, diasteriomer, racemic mixture, enantiomerically-enriched mixture, solvate, or prodrug of a compound according to Formula XXVII, in a pharmaceutically effective carrier; and which is present in an analgesically-effective amount, wherein each of $R_1$, $R_2$, $R_3$, $R_4$, $R_5$ and $R_6$ is independently H, OH, $OCH_3$, or a substituted or unsubstituted: alkyl; alkenyl; or alkynyl group; wherein each of $R_1$, $R_2$, $R_3$, $R_4$, $R_5$ and $R_6$ may be substituted at any unsubstituted position on its respective ring structure; wherein each of S and S' is independently a carbohydrate moiety; wherein at least one of S and S' is present, and the other of S and S' is optionally present; and wherein, when present, each of S and S' is bound to its respective ring structure through one of $R_1$, $R_2$, $R_3$, $R_4$, $R_5$, or $R_6$.

In any of the preceding or alternative embodiments, a compound according to Formula XXVII is a compound according to Formula XXVIII:

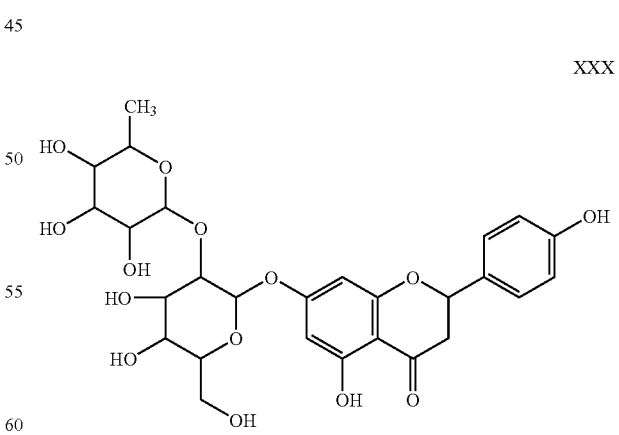

XXX

In any of the preceding or alternative embodiments, the present invention is directed to a pharmaceutical composition, comprising a therapeutically effective amount of a compound according to Formula XXXIII:

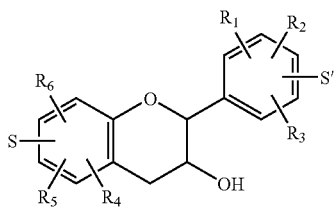

XXXIII or a pharmaceutically-acceptable salt, enantiomer, diastereomer, racemic mixture, enantiomerically-enriched mixture, solvate, or prodrug of a compound according to Formula XXXIII, in a pharmaceutically effective carrier; and which is present in an analgesically-effective amount, wherein each of $R_1$, $R_2$, $R_3$, $R_4$, $R_5$ and $R_6$ is independently H, OH, OCH$_3$, or a substituted or unsubstituted: alkyl; alkenyl; or alkynyl group; wherein each of $R_1$, $R_2$, $R_3$, $R_4$, $R_5$ and $R_6$ may be substituted at any unsubstituted position on its respective ring structure; wherein each of S and S' is independently a carbohydrate moiety; wherein at least one of S and S' is present, and the other of S and S' is optionally present; and wherein, when present, each of S and S' is bound to its respective ring structure through one of $R_1$, $R_2$, $R_3$, $R_4$, $R_5$, $R_6$, or the indicated 3-OH group.

In any of the preceding or alternative embodiments, a compound according to Formula XXXIII is a compound according to Formula XXXIV:

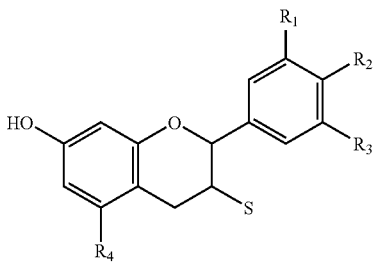

XXXIV wherein each of $R_1$, $R_2$, $R_3$, and $R_4$ is independently H, OH, OCH$_3$, or a substituted or unsubstituted: alkyl; alkenyl; or alkynyl group; and wherein S is a carbohydrate moiety.

In any of the preceding or alternative embodiments, the present invention is directed to a pharmaceutical composition, comprising a therapeutically effective amount of a compound according to Formula XXXVII:

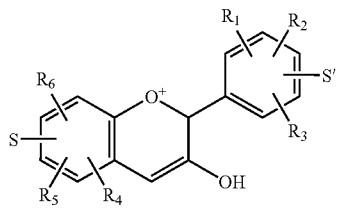

XXXVII or a pharmaceutically-acceptable salt, enantiomer, diastereomer, racemic mixture, enantiomerically-enriched mixture, solvate, or prodrug of a compound according to Formula XXXVII, in a pharmaceutically effective carrier; and which is present in an analgesically-effective amount, wherein each of $R_1$, $R_2$, $R_3$, $R_4$, $R_5$ and $R_6$ is independently H, OH, OCH$_3$, or a substituted or unsubstituted: alkyl; alkenyl; or alkynyl group; wherein each of $R_1$, $R_2$, $R_3$, $R_4$, $R_5$ and $R_6$ may be substituted at any unsubstituted position on its respective ring structure; wherein each of S and S' is independently a carbohydrate moiety; wherein at least one of S and S' is present, and the other of S and S' is optionally present; and wherein, when present, each of S and S' is bound to its respective ring structure through one of $R_1$, $R_2$, $R_3$, $R_4$, $R_5$, $R_6$, or the indicated 3-OH group.

In any of the preceding or alternative embodiments, a compound according to Formula XXXIII is a compound according to Formula XXXVIII:

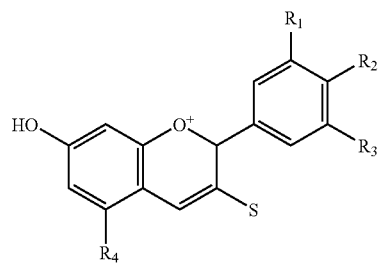

XXXVIII wherein each of $R_1$, $R_2$, $R_3$, and $R_4$ is independently H, OH, OCH$_3$, or a substituted or unsubstituted: alkyl; alkenyl; or alkynyl group; and wherein S is a carbohydrate moiety.

In any of the preceding or alternative embodiments, a compound according to Formula XXXIII is a compound according to Formula XXXIX:

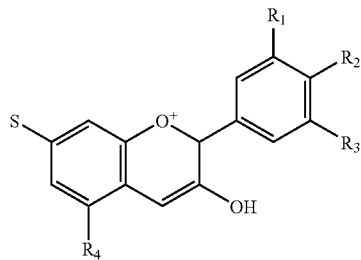

XXXIX wherein each of $R_1$, $R_2$, $R_3$, and $R_4$ is independently H, OH, OCH$_3$, or a substituted or unsubstituted: alkyl; alkenyl; or alkynyl group; and wherein S is a carbohydrate moiety.

In any of the preceding or alternative embodiments, the present invention is directed to pharmaceutical compositions, comprising a therapeutically effective amount of a flavonoid glycoside in a pharmaceutically effective carrier; wherein the flavonoid glycoside is present in an analgesically-effective amount. In one embodiment, the flavonoid glycoside comprises, for example and without limitation, an aglycone moiety selected from the group consisting of a Flavone (for example, Apigenin, Luteolin, Tangeritin, or Diosmetin); an Isoflavone (for example, Genistein, Daidzein, or Glycitein); a Flavonol (for example, Quercetin, Rutin, Kaempferol, Myricetin, Isorhamnetin, Pachypodol, or Rhamnazin); a Flavanone (for example, Hesperidin or Naringin), a Flavan-3-ol (for example, Catechin, Epicatechin, or Epigallocatechin), and an Anthocyanidin (for example, Cyanidin, Delphinidin, Malvidin, Pelargonidin, Peonidin, or Petunidin).

In any of the preceding or alternative embodiments, the present invention is directed to methods for effecting analgesia, treating pain, and/or treating discomfort in a mammal, comprising administering to a patient in need thereof a pharmaceutical composition comprising a therapeutically effective amount of a compound according to Formula IV:

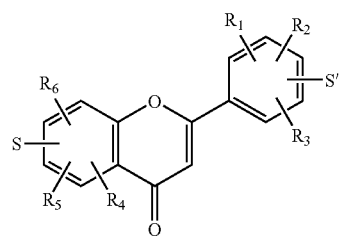

IV or a pharmaceutically-acceptable salt, enantiomer, diasteriomer, racemic mixture, enantiomerically-enriched mixture, solvate, or prodrug of a compound according to Formula IV, in a pharmaceutically effective carrier; and which is present in an analgesically-effective amount, wherein each of $R_1$, $R_2$, $R_3$, $R_4$, $R_5$ and $R_6$ is independently H, OH, $OCH_3$, or a substituted or unsubstituted: alkyl; alkenyl; or alkynyl group; wherein each of $R_1$, $R_2$, $R_3$, $R_4$, $R_5$ and $R_6$ may be substituted at any unsubstituted position on its respective ring structure; wherein each of S and S' is independently a carbohydrate moiety; wherein at least one of S and S' is present, and the other of S and S' is optionally present; and wherein, when present, each of S and S' is bound to its respective ring structure through one of $R_1$, $R_2$, $R_3$, $R_4$, $R_5$ or $R_6$.

In any of the preceding or alternative embodiments of such methods of the present invention, the compound according to Formula IV is a compound according to Formula V:

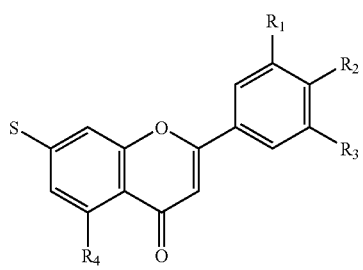

V wherein each of $R_1$, $R_2$, $R_3$, and $R_4$ is independently H, OH, $OCH_3$, or a substituted or unsubstituted: alkyl; alkenyl; or alkynyl group; and wherein S is a carbohydrate moiety.

In any of the preceding or alternative embodiments of such methods of the present invention, $R_1$ is H, $R_2$ is OH, $R_3$ is H, $R_4$ is OH; and S is a carbohydrate moiety, of the compound according to Formula V; and in another embodiment of such methods $R_1$ is OH, $R_2$ is OH, $R_3$ is H, $R_4$ is OH; and S is a carbohydrate moiety, of the compound according to Formula V.

In any of the preceding or alternative embodiments of such methods of the present invention, the compound according to Formula V is a compound according to Formula IX:

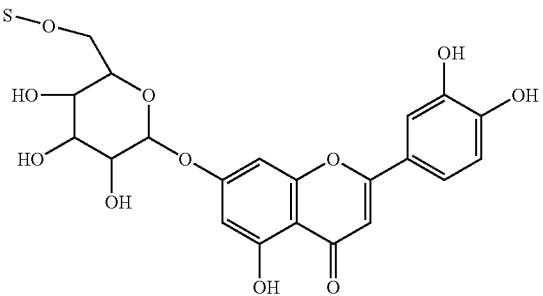

IX wherein S is a carbohydrate moiety.

In any of the preceding or alternative embodiments of such methods of the present invention, the compound according to Formula V is a compound of Formula X:

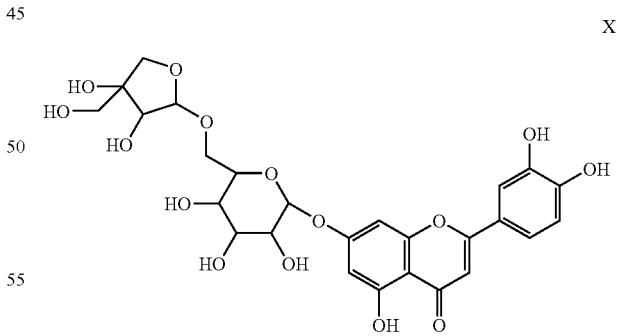

X

In any of the preceding or alternative embodiments, the present invention is directed to methods for providing therapeutic treatment to a mammal, comprising administering to a patient in need thereof a pharmaceutical composition comprising a therapeutically effective amount of a compound according to Formula X:

X or a pharmaceutically-acceptable salt, enantiomer, diasteriomer, racemic mixture, enantiomerically-enriched mixture, solvate, or prodrug of a compound of Formula X, in a pharmaceutically effective carrier.

In any of the preceding or alternative embodiments, the present invention is directed to methods for effecting analgesia, treating pain, and/or treating discomfort in a mammal, comprising administering to a patient in need thereof a pharmaceutical composition comprising a therapeutically effective amount of a compound according to Formula X:

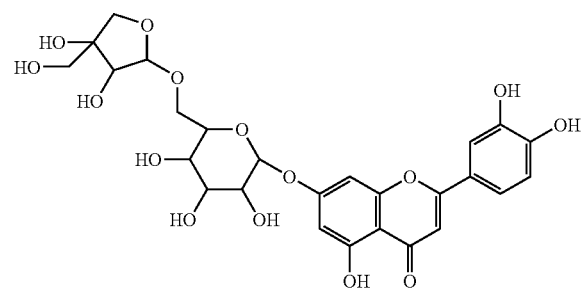

X or a pharmaceutically-acceptable salt, enantiomer, diasteriomer, racemic mixture, enantiomerically-enriched mixture, solvate, or prodrug of a compound of Formula X, in a pharmaceutically effective carrier; and which is present in an analgesically-effective amount.

In any of the preceding or alternative embodiments, the present invention is directed to methods for effecting analgesia, treating pain, and/or treating discomfort in a mammal, comprising administering to a patient in need thereof a pharmaceutical composition comprising a therapeutically effective amount of a compound according to: Formula XIII:

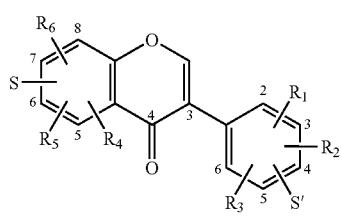

XIII or a pharmaceutically-acceptable salt, enantiomer, diasteriomer, racemic mixture, enantiomerically-enriched mixture, solvate, or prodrug of a compound of Formula XIII, in a pharmaceutically effective carrier; and which is present in an analgesically-effective amount, wherein each of $R_1$, $R_2$, $R_3$, $R_4$, $R_5$ and $R_6$ is independently H, OH, $OCH_3$, or a substituted or unsubstituted: alkyl; alkenyl; or alkynyl group; and wherein each of $R_1$, $R_2$, $R_3$, $R_4$, $R_5$ and $R_6$ may be substituted at any unsubstituted position on its respective ring structure; and wherein each of S and S' is independently a carbohydrate moiety; and wherein at least one of S and S' is present, and the other of S and S' is optionally present; and wherein, when present, each of S and S' is bound to its respective ring structure through one of $R_1$, $R_2$, $R_3$, $R_4$, $R_5$ or $R_6$;

a compound according to Formula XIX:

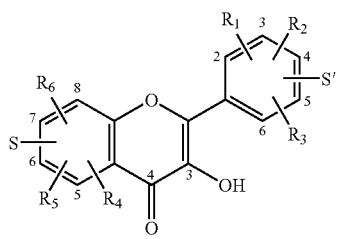

XIX or a pharmaceutically-acceptable salt, enantiomer, diasteriomer, racemic mixture, enantiomerically-enriched mixture, solvate, or prodrug of a compound of Formula XIX, in a pharmaceutically effective carrier; and which is present in an analgesically-effective amount, wherein each of $R_1$, $R_2$, $R_3$, $R_4$, $R_5$ and $R_6$ is independently H, OH, $OCH_3$, or a substituted or unsubstituted: alkyl; alkenyl; or alkynyl group; and wherein each of $R_1$, $R_2$, $R_3$, $R_4$, $R_5$ and $R_6$ may be substituted at any unsubstituted position on its respective ring structure; and wherein each of S and S' is independently a carbohydrate moiety; and wherein at least one of S and S' is present, and the other of S and S' is optionally present; and wherein, when present, each of S and S' is bound to its respective ring structure through one of $R_1$, $R_2$, $R_3$, $R_4$, $R_5$, $R_6$, or the indicated 3-OH group;

a compound according to Formula XXVII:

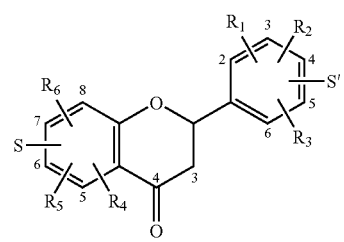

XXVII or a pharmaceutically-acceptable salt, enantiomer, diasteriomer, racemic mixture, enantiomerically-enriched mixture, solvate, or prodrug of a compound of Formula XXVII, in a pharmaceutically effective carrier; and which is present in an analgesically-effective amount, wherein each of $R_1$, $R_2$, $R_3$, $R_4$, $R_5$ and $R_6$ is independently H, OH, $OCH_3$, or a substituted or unsubstituted: alkyl; alkenyl; or alkynyl group; and wherein each of $R_1$, $R_2$, $R_3$, $R_4$, $R_5$ and $R_6$ may be substituted at any unsubstituted position on its respective ring structure; and wherein each of S and S' is independently a carbohydrate moiety; and wherein at least one of S and S' is present, and the other of S and S' is optionally present; and wherein, when present, each of S and S' is bound to its respective ring structure through one of $R_1$, $R_2$, $R_3$, $R_4$, $R_5$ or $R_6$;

a compound according to Formula XXXIII:

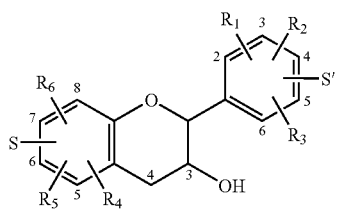

XXXIII or a pharmaceutically-acceptable salt, enantiomer, diasteriomer, racemic mixture, enantiomerically-enriched mixture, solvate, or prodrug of a compound of Formula XXXIII, in a pharmaceutically effective carrier; and which is present in an analgesically-effective amount, wherein each of $R_1$, $R_2$, $R_3$, $R_4$, $R_5$ and $R_6$ is independently H, OH, $OCH_3$, or a substituted or unsubstituted: alkyl; alkenyl; or alkynyl group; and wherein each of $R_1$, $R_2$, $R_3$, $R_4$, $R_5$ and $R_6$ may be substituted at any unsubstituted position on its respective ring structure; and wherein each of S and S' is independently a carbohydrate moiety; and wherein at least one of S and S' is present, and the other of S and S' is optionally present; and wherein, when present, each of S and S' is bound to its respective ring structure through one of $R_1$, $R_2$, $R_3$, $R_4$, $R_5$, $R_6$, or the indicated 3-OH group;

or a compound according to Formula XXXVII:

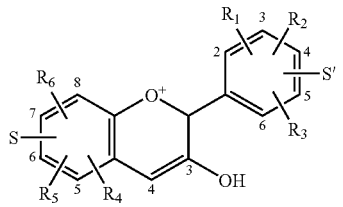

XXXVII or a pharmaceutically-acceptable salt, enantiomer, diasteriomer, racemic mixture, enantiomerically-enriched mixture, solvate, or prodrug of a compound of Formula XXXVII, in a pharmaceutically effective carrier; and which is present in an analgesically-effective amount, wherein each of $R_1$, $R_2$, $R_3$, $R_4$, $R_5$ and $R_6$ is independently H, OH, $OCH_3$, or a substituted or unsubstituted: alkyl; alkenyl; or alkynyl group; and wherein each of $R_1$, $R_2$, $R_3$, $R_4$, $R_5$ and $R_6$ may be substituted at any unsubstituted position on its respective ring structure; and wherein each of S and S' is independently a carbohydrate moiety; and wherein at least one of S and S' is present, and the other of S and S' is optionally present; and wherein, when present, each of S and S' is bound to its respective ring structure through one of $R_1$, $R_2$, $R_3$, $R_4$, $R_5$, $R_6$, or the indicated 3-OH group.

In any of the preceding or alternative embodiments, the present invention is directed to methods for effecting analgesia, treating pain, and/or treating discomfort in a mammal, comprising administering to a patient in need thereof a pharmaceutical composition comprising a therapeutically effective amount of a compound according to: Formula XIV:

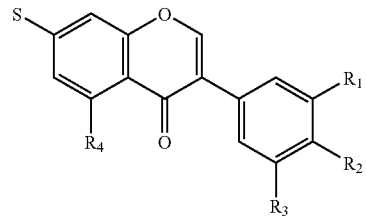

XIV or a pharmaceutically-acceptable salt, enantiomer, diasteriomer, racemic mixture, enantiomerically-enriched mixture, solvate, or prodrug of a compound of Formula XIV, in a pharmaceutically effective carrier; and which is present in an analgesically-effective amount, wherein each of $R_1$, $R_2$, $R_3$, and $R_4$ is independently H, OH, $OCH_3$, or a substituted or unsubstituted: alkyl; alkenyl; or alkynyl group; and wherein S is a carbohydrate moiety;

a compound according to Formula XX:

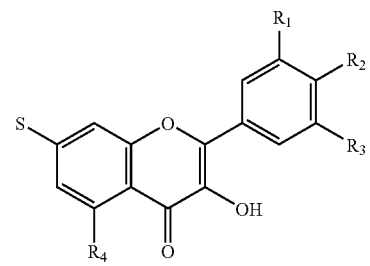

XX or a pharmaceutically-acceptable salt, enantiomer, diasteriomer, racemic mixture, enantiomerically-enriched mixture, solvate, or prodrug of a compound of Formula XX, in a pharmaceutically effective carrier; and which is present in an analgesically-effective amount, wherein each of $R_1$, $R_2$, $R_3$, and $R_4$ is independently H, OH, $OCH_3$, or a substituted or unsubstituted: alkyl; alkenyl; or alkynyl group; and wherein S is a carbohydrate moiety; a compound according to Formula XXVIII:

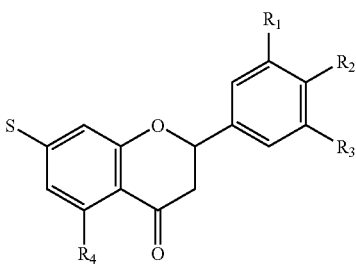

XXVIII or a pharmaceutically-acceptable salt, enantiomer, diasteriomer, racemic mixture, enantiomerically-enriched mixture, solvate, or prodrug of a compound of Formula XXVIII, in a pharmaceutically effective carrier; and which is present in an analgesically-effective amount, wherein each of $R_1$, $R_2$, $R_3$, and $R_4$ is independently H, OH, $OCH_3$, or a substituted or unsubstituted: alkyl; alkenyl; or alkynyl group; and wherein S is a carbohydrate moiety;

a compound according to Formula XXXIV:

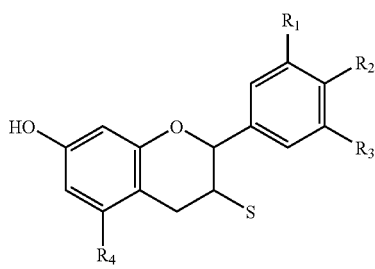

XXXIV or a pharmaceutically-acceptable salt, enantiomer, diasteriomer, racemic mixture, enantiomerically-enriched mixture, solvate, or prodrug of a compound of Formula XXXIV, in a pharmaceutically effective carrier; and which is present in an analgesically-effective amount, wherein each of $R_1$, $R_2$, $R_3$, and $R_4$ is independently H, OH, $OCH_3$, or a substituted or unsubstituted: alkyl; alkenyl; or alkynyl group; and wherein S is a carbohydrate moiety;

a compound according to Formula XXXVIII:

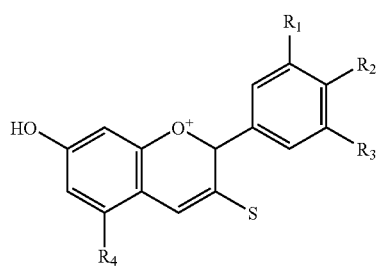

XXXVIII or a pharmaceutically-acceptable salt, enantiomer, diasteriomer, racemic mixture, enantiomerically-enriched mixture, solvate, or prodrug of a compound of Formula XXXVIII, in a pharmaceutically effective carrier; and which is present in an analgesically-effective amount, wherein each of $R_1$, $R_2$, $R_3$, and $R_4$ is independently H, OH, $OCH_3$, or a substituted or unsubstituted: alkyl; alkenyl; or alkynyl group; and wherein S is a carbohydrate moiety;

or a compound according to Formula XXXIX:

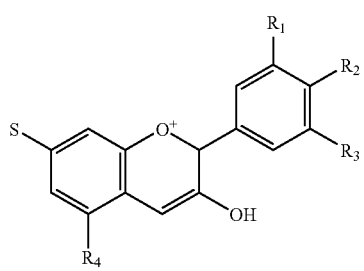

XXXIX or a pharmaceutically-acceptable salt, enantiomer, diasteriomer, racemic mixture, enantiomerically-enriched mixture, solvate, or prodrug of a compound of Formula XXXIX, in a pharmaceutically effective carrier; and which is present in an analgesically-effective amount, wherein each of $R_1$, $R_2$, $R_3$, and $R_4$ is independently H, OH, $OCH_3$, or a substituted or unsubstituted: alkyl; alkenyl; or alkynyl group; and wherein S is a carbohydrate moiety.

In any of the preceding or alternative embodiments, the present invention is directed to methods for reducing inflammation in a mammal, comprising administering to a patient in need thereof a pharmaceutical composition comprising a therapeutically effective amount of a compound according to Formula X:

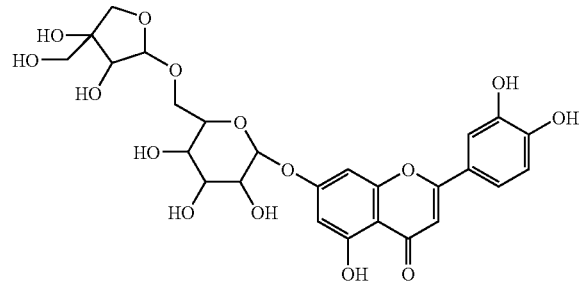

X or a pharmaceutically-acceptable salt, enantiomer, diasteriomer, racemic mixture, enantiomerically-enriched mixture, solvate, or prodrug of a compound of Formula X, in a pharmaceutically effective carrier.

In any of the preceding or alternative embodiments, the present invention is directed to methods for treating a patient, comprising administering to a patient in need thereof a pharmaceutical composition comprising a therapeutically effective amount of a compound according to Formula X:

X or a pharmaceutically-acceptable salt, enantiomer, diasteriomer, racemic mixture, enantiomerically-enriched mixture, solvate, or prodrug of a compound of Formula X, in a pharmaceutically effective carrier, wherein the treatment is for a condition selected from the group consisting of: fever; rheumatic fever; symptoms associated with influenza or other viral infections; common cold; low back and neck pain; dysmenorrhea; headache; toothache; sprains and strains; myositis; neuralgia; synovitis; arthritis, rheumatoid arthritis; degenerative joint diseases, including osteoarthritis; gout; ankylosing spondylitis; bursitis; burns; injuries; and pain and inflammation following surgical and dental procedures.

DETAILED DESCRIPTION OF CERTAIN EMBODIMENTS

Figure 1:
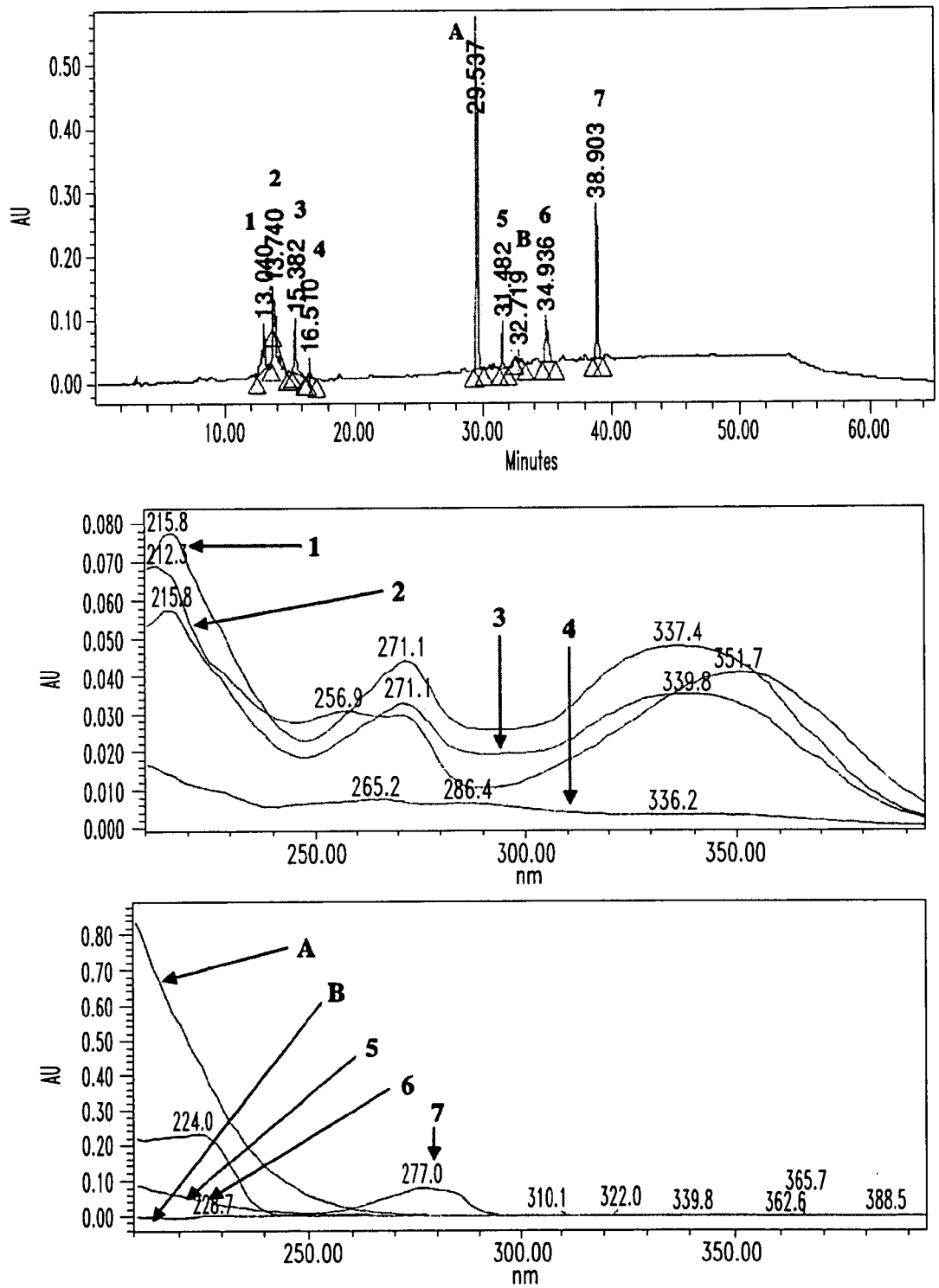
FIG. 1: HPLC chromatograms and UV spectra of BMBW-M40i peaks from Example 4.

The present invention is directed to the discovery that certain flavonoid glycoside-type compounds are useful as therapeutic agents for a variety of therapeutic uses; and in particular as analgesics and anti-inflammatories for the prevention, treatment and management of pain and inflammatory conditions. As described herein, such compounds have been isolated, purified, identified, and shown to have therapeutic utility. The identification and characterization of such compounds, pharmaceutical compositions including such compounds, and methods of making and using such compounds and pharmaceutical compositions of the present invention, are the result of research efforts described herein that stem from the unexpected discovery that the puree or juice of sweet peppers exhibits an analgesic effect on inflamed pharyngeal mucosa, without the burning sensation or pungency that accompanies the use of capsaicin or the purees or juices of peppers exhibiting pungency.

Flavonoid glycoside compounds that exhibit therapeutic activity and may be used in the present invention generally include a flavonoid aglycone moiety bound to a glycone moiety. The general chemical structure of flavonoids is based on a $C_{15}$ skeleton having a chromane ring bearing a second aromatic ring, as shown in Formula I:

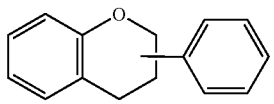

I

Flavonoids are generally classified into subgroups according to substitution patterns of compounds according to Formula I. Described and discussed herein are certain flavonoid glycosides shown to be therapeutically active in the present invention, as well as certain flavonoid glycosides which may be determined by one of skill in the art as therapeutically active and suitable for use in the present invention using the teachings provided herein. Further, the present invention is not limited to those compounds disclosed herein, but also includes all flavonoid glycoside compounds which exhibit therapeutic activity; the efficacy and structure of which compounds may likewise be determined by one of skill in the art using the teachings provided herein.

In this regard, the present invention is directed in certain embodiments to pharmaceutical compositions that include therapeutically effective, and in particular analgesically effective, compounds from various Flavonoid subgroups, for example and without limitation: Flavones; Isoflavones; Flavonols; Flavanones; Flavan-3-ols; and Anthocyanidins, as discussed herein.

Flavones

Flavones have a chemical structure generally defined by a 2-phenyl-4H-1-benzopyran-4-one skeleton, and any Flavone having such a skeleton may be used as the aglycone in Flavone glycosides of the present invention that exhibits therapeutic activity, including compounds according to Formula II:

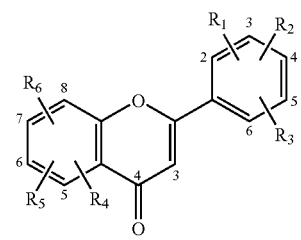

II wherein each of $R_1$, $R_2$, $R_3$, $R_4$, $R_5$ and $R_6$ is independently H, OH, OCH$_3$; or a substituted or unsubstituted: alkyl; alkenyl; or alkynyl group; and wherein each of $R_1$, $R_2$, $R_3$, $R_4$, $R_5$ and $R_6$ may be substituted at any unsubstituted position on their respective ring structures.

Flavones which may be used as the aglycone in flavonoid glycosides of the present invention that exhibits therapeutic activity include, for example and without limitation, compounds according to Formula III:

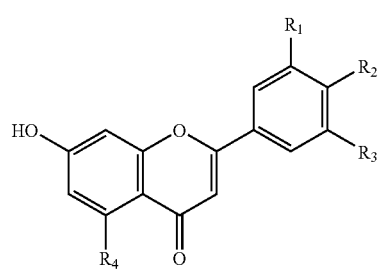

III wherein each of $R_1$, $R_2$, $R_3$, and $R_4$ is as defined previously.

Flavone glycosides which may be suitable for use in the present invention include, for example and without limitation, compounds according to Formula IV:

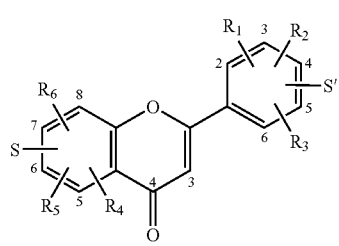

IV wherein each of $R_1$, $R_2$, $R_3$, $R_4$, $R_5$ and $R_6$ is independently H, OH, OCH$_3$, or a substituted or unsubstituted: alkyl; alkenyl; or alkynyl group; and wherein each of $R_1$, $R_2$, $R_3$, $R_4$, $R_5$ and $R_6$ may be substituted at any unsubstituted position on its respective ring structure; and wherein each of S and S' is independently a carbohydrate moiety selected from, for example and without limitation, the group consisting of substituted and unsubstituted: monosaccharides, such as glucose, fructose, galactose, rhamnose, xylose or arabinose; substituted and unsubstituted disaccharides, such as sucrose, maltose, or lactose; substituted and unsubstituted trisaccharides; substituted and unsubstituted oligosaccharides; and an apiofuranosyl-glucopyranosyl moiety; and wherein at least one of S and S' is present, and the other of S and S' is optionally present; and wherein, when present, each of S and S' is bound to its respective ring structure through one of $R_1$, $R_2$, $R_3$, $R_4$, $R_5$ or $R_6$.

As will be appreciated by one of skill in the art, the above list is illustrative only and by no means exhaustive, and any carbohydrate moiety may be used in compounds of the present invention that exhibit therapeutic activity.

Flavone glycosides which may be suitable for use in the present invention include, for example and without limitation, compounds according to Formula V:

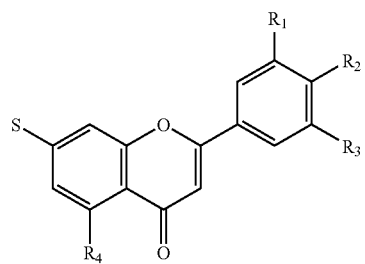

V wherein each of $R_1$, $R_2$, $R_3$, and $R_4$ is as previously defined; and wherein S is as previously defined.

Flavone glycosides which may be suitable for use in the present invention include, for example and without limitation: (1) Apigenin glycosides according to, (a) Formula VI:

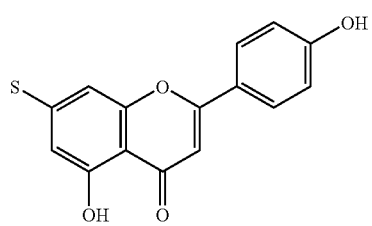

VI wherein S is as previously defined, and (b) Formula VII:

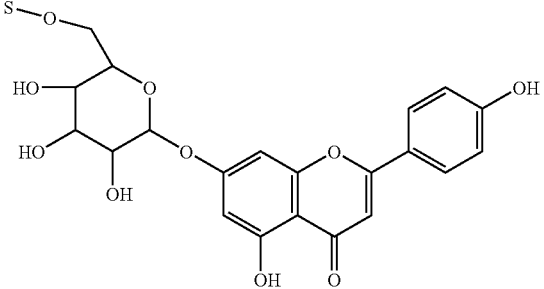

VII wherein S is as previously defined; and (2) Luteolin glycosides according to (a) Formula Va:

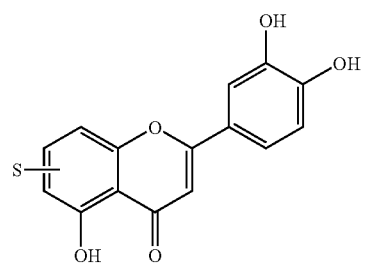

Va wherein S is as previously defined; (b) Formula VIII:

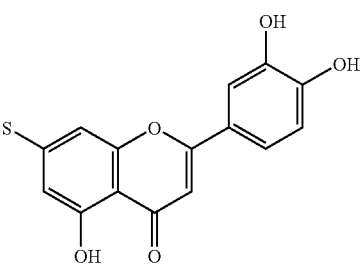

VIII wherein S is as previously defined, and (c) Formula IX:

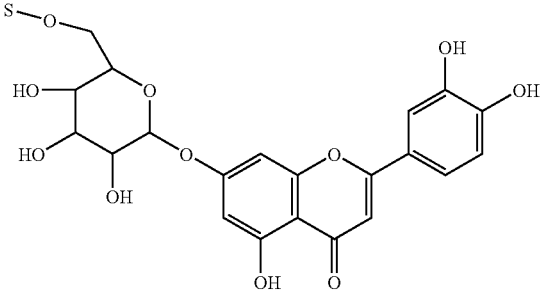

IX wherein S is as previously defined.

A specific Luteolin glycoside shown herein to be suitable for use in the present invention includes a compound of Formula X (Compound 580), which is shown in a particular structural conformation in Formula $X_1$:

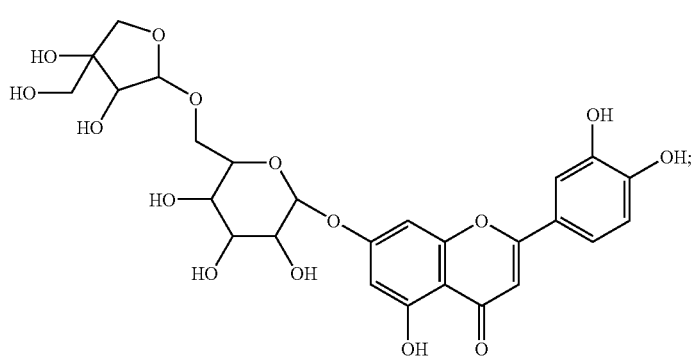

Compound 580

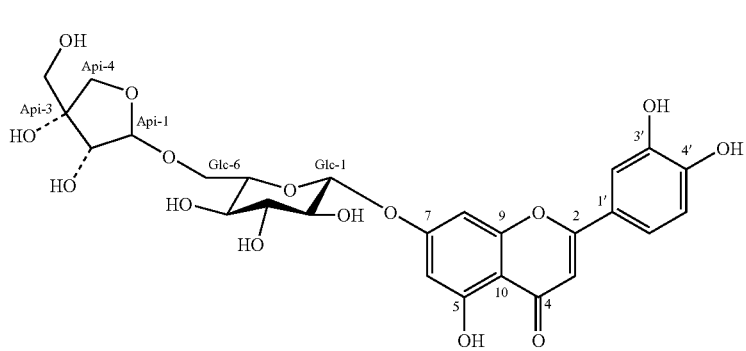

Moreover, as will be appreciated by one of skill in the art, the Flavone glycosides shown herein are only exemplary of those which are known to be suitable for use, or which may be used, in the present invention, and in no way limits the scope of the present invention. Any Flavone glycoside that exhibits therapeutic activity may be used in the present invention. The suitability of a particular Flavone glycoside may be determined, for example, by bioassaying the compound according to the protocol set forth in Example 1.

For example and without limitation, additional Flavones which may be used as the aglycone in Flavone glycosides of the present invention that exhibits therapeutic activity include Tangeritin and Diosmetin.

Also, Flavone glycosides that may be used in the present invention may be substituted with suitable moieties in place of, or in addition to, those shown in the described compounds, so long as the Flavone glycoside exhibits therapeutic activity. Likewise, the position of the carbohydrate (S) moiety in the described compounds is exemplary only, and in no way limits the scope of the present invention. For example, the carbohydrate (S) moiety may be bound to the aglycone moiety through any suitable group thereon which permits formation of an acetal or other suitable linkage.

Isoflavones

Isoflavones have a chemical structure generally defined by a 3-phenyl-4H-1-benzopyran-4-one skeleton, and include compounds according to Formula XI:

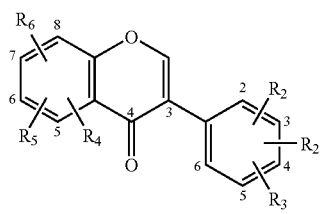

wherein each of $R_1$, $R_2$, $R_3$, $R_4$, $R_5$ and $R_6$ is independently H, OH, OCH$_3$; or a substituted or unsubstituted: alkyl; alkenyl; or alkynyl group; and wherein each of $R_1$, $R_2$, $R_3$, $R_4$, $R_5$ and $R_6$ may be substituted at any unsubstituted position on their respective ring structures.

Isoflavones which may be suitable for use as the aglycone in isoflavonoid glycosides of the present invention include, for example and without limitation, compounds according to Formula XII:

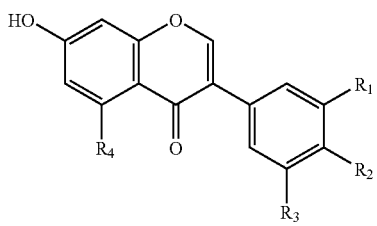

XII wherein each of $R_1$, $R_2$, $R_3$, and $R_4$ is as defined previously.

Isoflavone glycosides which may be suitable for use in the present invention include, for example and without limitation, compounds according to Formula XIII:

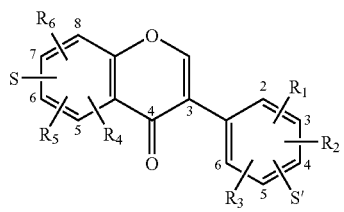

XIII wherein each of $R_1$, $R_2$, $R_3$, $R_4$, $R_5$ and $R_6$ is independently H, OH, $OCH_3$, or a substituted or unsubstituted: alkyl; alkenyl; or alkynyl group; and wherein each of $R_1$, $R_2$, $R_3$, $R_4$, $R_5$ and $R_6$ may be substituted at any unsubstituted position on its respective ring structure; and wherein each of S and S' is independently a carbohydrate moiety selected from, for example and without limitation, the group consisting of substituted and unsubstituted: monosaccharides, such as glucose, fructose, galactose, rhamnose, xylose or arabinose; substituted and unsubstituted disaccharides, such as sucrose, maltose, or lactose; substituted and unsubstituted trisaccharides; substituted and unsubstituted oligosaccharides; and an apiofuranosyl-glucopyranosyl moiety; and wherein at least one of S and S' is present, and the other of S and S' is optionally present; and wherein, when present, each of S and S' is bound to its respective ring structure through one of $R_1$, $R_2$, $R_3$, $R_4$, $R_5$ or $R_6$.

As will be appreciated by one of skill in the art, the above list is illustrative only and by no means exhaustive, and any carbohydrate moiety may be used in compounds of the present invention that exhibits therapeutic activity.

Isoflavone glycosides which may be suitable for use in the present invention include, for example and without limitation, compounds according to Formula XIV:

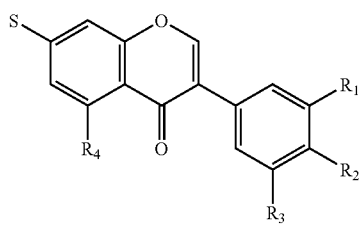

XIV wherein each of $R_1$, $R_2$, $R_3$, and $R_4$ is as previously defined; and wherein S is as previously defined.

Isoflavone glycosides which may be used in the present invention in compounds that exhibit therapeutic activity include, for example and without limitation: (1) Genistein glycosides according to, Formula XV: (isomer of Apigenin glycosides)

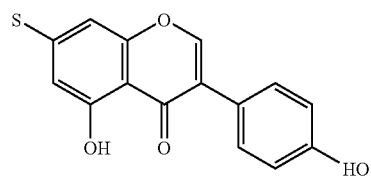

XV wherein S is as previously defined; (2) Daidzein glycosides; and (3) Glycitein glycosides.

A Luteolin glycoside isomer that may be suitable for use in the present invention is a compound of Formula XVI:

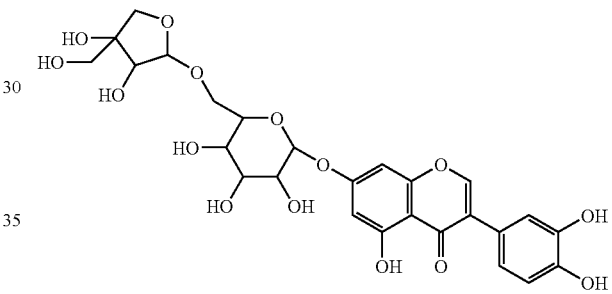

XVI

Moreover, as will be appreciated by one of skill in the art, the Isoflavone glycosides shown herein are only exemplary of those which are known to be suitable for use, or which may be used, in the present invention, and in no way limits the scope of the present invention. Any Isoflavone glycoside that exhibits therapeutic activity may be used in the present invention. The suitability of a particular Isoflavone glycoside may be determined, for example, by bioassaying the compound according to the protocol set forth in Example 1.

Also, Isoflavone glycosides that may be used in the present invention may be substituted with suitable moieties in place of, or in addition to, those shown in the described compounds, so long as the Isoflavone glycoside exhibits therapeutic activity. Likewise, the position of the carbohydrate (S) moiety in the described compounds is exemplary only, and in no way limits the scope of the present invention. For example, the carbohydrate (S) moiety may be bound to the aglycone moiety through any suitable group thereon which permits formation of an acetal or other suitable linkage.

Flavonols

Flavonols have a chemical structure generally defined by a 3-hydroxy-2-phenyl-4H-1-benzopyran-4-one skeleton, and any Flavonol having such a skeleton may be used as the aglycone in Flavonol glycosides of the present invention that exhibit therapeutic activity, including compounds according to Formula XVII:

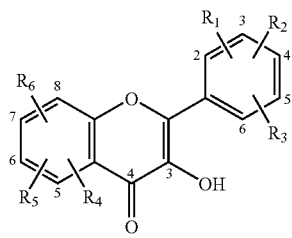

XVII wherein each of $R_1$, $R_2$, $R_3$, $R_4$, $R_5$ and $R_6$ is independently H, OH, OCH$_3$; or a substituted or unsubstituted: alkyl; alkenyl; or alkynyl group; and wherein each of $R_1$, $R_2$, $R_3$, $R_4$, $R_5$ and $R_6$ may be substituted at any unsubstituted position on their respective ring structures.

Flavonols which may be used as the aglycone in flavonoid glycosides of the present invention that exhibit therapeutic activity include, for example and without limitation, compounds according to Formula XVIII:

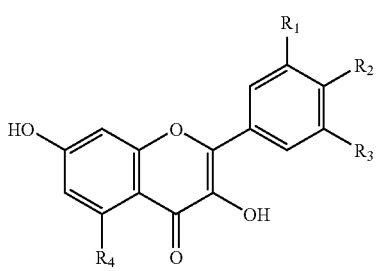

XVIII wherein each of $R_1$, $R_2$, $R_3$, and $R_4$ is as defined previously.

Flavonol glycosides which may be suitable for use in the present invention include, for example and without limitation, compounds according to Formula XIX:

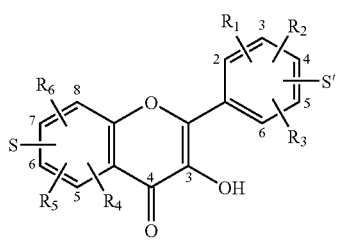

XIX wherein each of $R_1$, $R_2$, $R_3$, $R_4$, $R_5$ and $R_6$ is independently H, OH, OCH$_3$, or a substituted or unsubstituted: alkyl; alkenyl; or alkynyl group; and wherein each of $R_1$, $R_2$, $R_3$, $R_4$, $R_5$ and $R_6$ may be substituted at any unsubstituted position on its respective ring structure; and wherein each of S and S' is independently a carbohydrate moiety selected from, for example and without limitation, the group consisting of substituted and unsubstituted: monosaccharides, such as glucose, fructose, galactose, rhamnose, xylose or arabinose; substituted and unsubstituted disaccharides, such as sucrose, maltose, or lactose; substituted and unsubstituted trisaccharides; substituted and unsubstituted oligosaccharides; and an apiofuranosyl-glucopyranosyl moiety; and wherein at least one of S and S' is present, and the other of S and S' is optionally present; and wherein, when present, each of S and S' is bound to its respective ring structure through one of $R_1$, $R_2$, $R_3$, $R_4$, $R_5$, $R_6$, or the indicated 3-OH group.

As will be appreciated by one of skill in the art, the above list is illustrative only and by no means exhaustive, and any carbohydrate moiety may be used in compounds of the present invention that exhibit therapeutic activity.

Flavonol glycosides which may be suitable for use in the present invention include, for example and without limitation, compounds according to Formula XX:

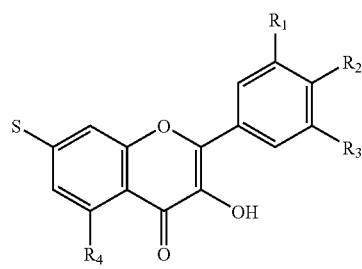

XX wherein each of $R_1$, $R_2$, $R_3$, and $R_4$ is as previously defined; and wherein S is as previously defined; and compounds according to Formula XXI:

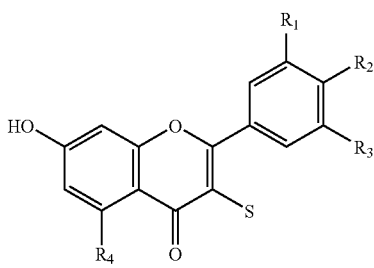

XXI wherein each of $R_1$, $R_2$, $R_3$, and $R_4$ is as previously defined; and wherein S is as previously defined.

Specific Flavonol glycosides according to Formula XXI which may be used in compounds having therapeutic activity in the present invention include Quercetin glycosides according to Formula XXII:

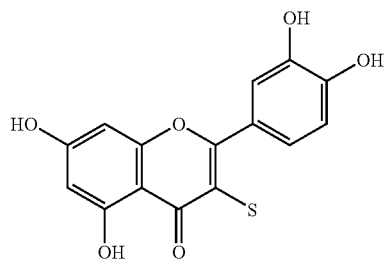

XXII such as Quercitrin (glycone: Rhamnose), shown in Formula XXIII:

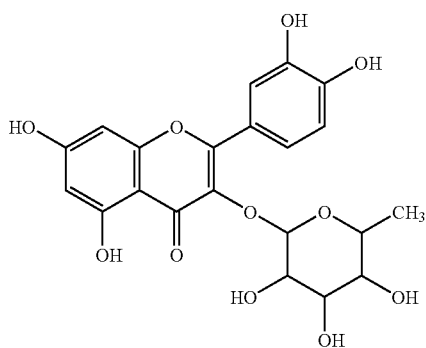

XXIII and Rutin (glycone: Rutinose), shown in Formula XXIV:

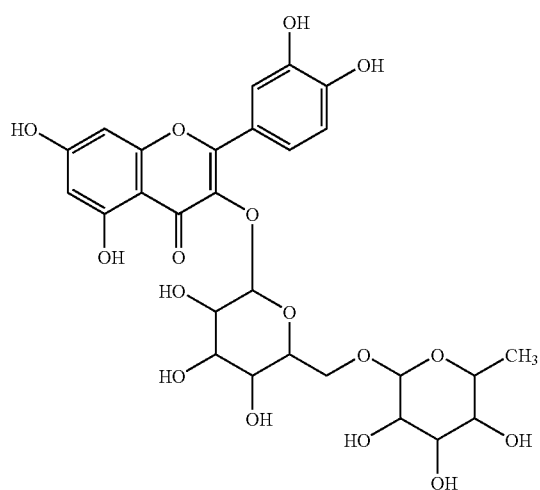

XXIV

Moreover, as will be appreciated by one of skill in the art, the Flavonol glycosides shown herein are only exemplary of those which are known to be suitable for use, or which may be used, in the present invention, and in no way limits the scope of the present invention. Any Flavonol glycoside that exhibits therapeutic activity may be used in the present invention. The suitability of a particular Flavonol glycoside may be determined, for example, by bioassaying the compound according to the protocol set forth in Example 1.

For example and without limitation, additional Flavonols which may be used as the aglycone in Flavonol glycosides of the present invention that exhibits therapeutic activity include Kaempferol, Myricetin, Isorhamnetin, Pachypodol, and Rhamnazin.

Also, Flavonol glycosides used in the present invention may be substituted with suitable moieties in place of, or in addition to, those shown in the described compounds, so long as the Flavonol glycoside exhibits therapeutic activity. Likewise, the position of the carbohydrate (S) moiety in the described compounds is exemplary only, and in no way limits the scope of the present invention. For example, the carbohydrate (S) moiety may be bound to the aglycone moiety through any suitable group thereon which permits formation of an acetal or other suitable linkage.

Flavanones

Flavanones have a chemical structure generally defined by a 2,3-dihydro-2-phenyl-4H-1-benzopyran-4-one skeleton, and any Flavanone having such a skeleton may be used as the aglycone in Flavanone glycosides of the present invention that exhibits therapeutic activity, including compounds according to Formula XXV:

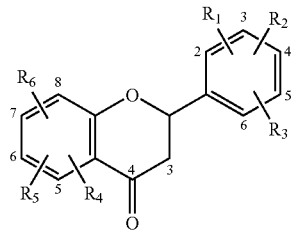

XXV wherein each of $R_1$, $R_2$, $R_3$, $R_4$, $R_5$ and $R_6$ is independently H, OH, $OCH_3$; or a substituted or unsubstituted: alkyl; alkenyl; or alkynyl group; and wherein each of $R_1$, $R_2$, $R_3$, $R_4$, $R_5$ and $R_6$ may be substituted at any unsubstituted position on their respective ring structures.

Flavanones which may be used as the aglycone in flavonoid glycosides exhibiting therapeutic activity in the present invention include, for example and without limitation, compounds according to Formula XXVI:

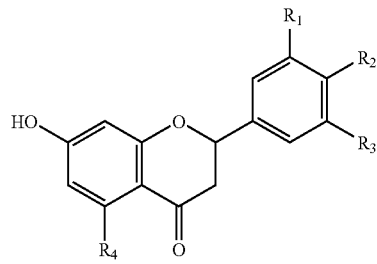

XXVI wherein each of $R_1$, $R_2$, $R_3$, and $R_4$ is as defined previously.

Flavanone glycosides which may be suitable for use in the present invention include, for example and without limitation, compounds according to Formula XXVII:

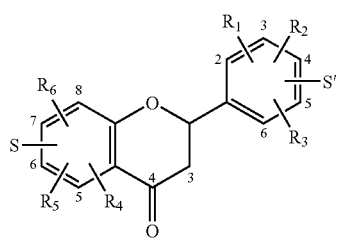

XXVII wherein each of $R_1$, $R_2$, $R_3$, $R_4$, $R_5$ and $R_6$ is independently H, OH, $OCH_3$, or a substituted or unsubstituted: alkyl; alkenyl; or alkynyl group; and wherein each of $R_1$, $R_2$, $R_3$, $R_4$, $R_5$ and $R_6$ may be substituted at any unsubstituted position on its respective ring structure; and wherein each of S and S' is independently a carbohydrate moiety selected from, for example and without limitation, the group consisting of substituted and unsubstituted: monosaccharides, such as glucose, fructose, galactose, rhamnose, xylose or arabinose; substituted and unsubstituted disaccharides, such as sucrose, maltose, or lactose; substituted and unsubstituted trisaccharides; substituted and unsubstituted oligosaccharides; and an apiofuranosyl-glucopyranosyl moiety; and wherein at least one of S and S' is present, and the other of S and S' is optionally present; and wherein, when present, each of S and S' is bound to its respective ring structure through one of $R_1$, $R_2$, $R_3$, $R_4$, $R_5$ or $R_6$.

As will be appreciated by one of skill in the art, the above list is illustrative only and by no means exhaustive, and any carbohydrate moiety may be used in compounds of the present invention that results in Flavanone glycosides with the intended therapeutic activity.

Flavanone glycosides which may be suitable for use in the present invention include, for example and without limitation, compounds according to Formula XXVIII:

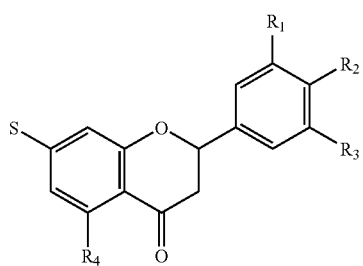

XXVIII wherein each of $R_1$, $R_2$, $R_3$, and $R_4$ is as previously defined; and wherein S is as previously defined.

Specific Flavanone glycosides that may be used in the present invention include Hesperidin (aglycone: Hesperetin, glycone: Rutinose), shown in Formula XXIX:

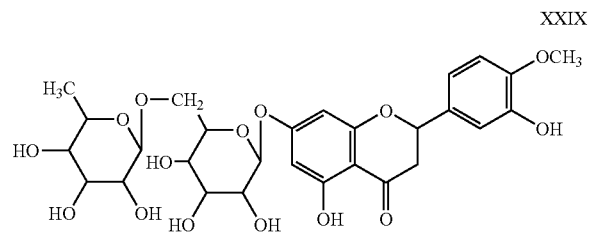

XXIX and Naringin (aglycone: Naringenin, glycone: Rutinose), shown in Formula XXX:

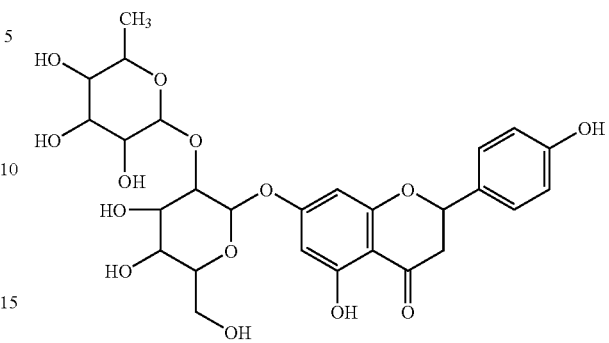

XXX

Moreover, as will be appreciated by one of skill in the art, the Flavanone glycosides shown herein are only exemplary of those which are known to be suitable for use, or which may be used, in the present invention, and in no way limits the scope of the present invention. Any Flavanone glycoside that exhibits therapeutic activity may be used in the present invention. The suitability of a particular Flavanone glycoside may be determined, for example, by bioassaying the compound according to the protocol set forth in Example 1.

For example and without limitation, an additional Flavanone which may be used as the aglycone in Flavanone glycosides of the present invention that exhibits therapeutic activity include Eriodictyol.

Also, Flavanone glycosides that may be used in the present invention may be substituted with suitable moieties in place of, or in addition to, those shown in the described compounds, so long as the Flavanone glycoside exhibits therapeutic activity. Likewise, the position of the carbohydrate (S) moiety in the described compounds is exemplary only, and in no way limits the scope of the present invention. For example, the carbohydrate (S) moiety may be bound to the aglycone moiety through any suitable group thereon which permits formation of an acetal or other suitable linkage.

Flavan-3-ols

Flavan-3-ols have a chemical structure generally defined by a 2,3-dihydro-3-hydroxy-2-phenyl-benzopyran skeleton, and any flavan-3-ol having such a skeleton may be used as the aglycone in flavan-3-ol glycosides of the present invention that exhibits therapeutic activity, including compounds according to Formula XXXI:

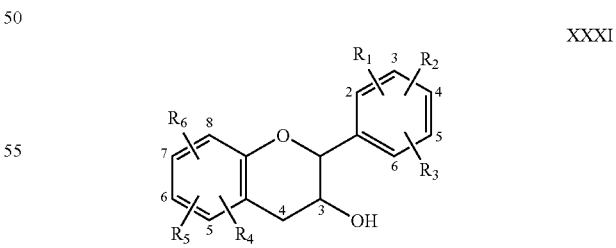

XXXI wherein each of $R_1$, $R_2$, $R_3$, $R_4$, $R_5$ and $R_6$ is independently H, OH, $OCH_3$; or a substituted or unsubstituted: alkyl; alkenyl; or alkynyl group; and wherein each of $R_1$, $R_2$, $R_3$, $R_4$, $R_5$ and $R_6$ may be substituted at any unsubstituted position on their respective ring structures.

Flavan-3-ols which may be used as the aglycone in flavonoid glycosides that exhibit therapeutic activity in the present invention include, for example and without limitation, compounds according to Formula XXXII:

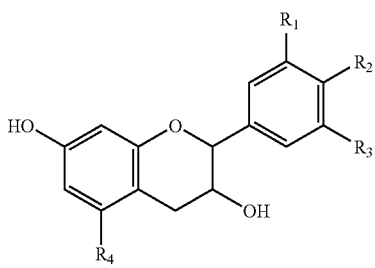

wherein each of $R_1$, $R_2$, $R_3$, and $R_4$ is as defined previously.

Flavan-3-ol glycosides which may be suitable for use in the present invention include, for example and without limitation, compounds according to Formula XXXIII:

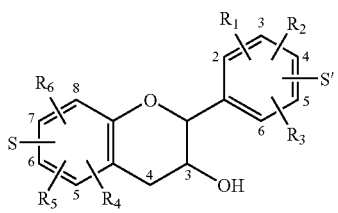

wherein each of $R_1$, $R_2$, $R_3$, $R_4$, $R_5$ and $R_6$ is independently H, OH, OCH$_3$, or a substituted or unsubstituted: alkyl; alkenyl; or alkynyl group; and wherein each of $R_1$, $R_2$, $R_3$, $R_4$, $R_5$ and $R_6$ may be substituted at any unsubstituted position on its respective ring structure; and wherein each of S and S' is independently a carbohydrate moiety selected from, for example and without limitation, the group consisting of substituted and unsubstituted: monosaccharides, such as glucose, fructose, galactose, rhamnose, xylose or arabinose; substituted and unsubstituted disaccharides, such as sucrose, maltose, or lactose; substituted and unsubstituted trisaccharides; substituted and unsubstituted oligosaccharides; and an apiofuranosyl-glucopyranosyl moiety; and wherein at least one of S and S' is present, and the other of S and S' is optionally present; and wherein, when present, each of S and S' is bound to its respective ring structure through one of $R_1$, $R_2$, $R_3$, $R_4$, $R_5$, $R_6$, or the indicated 3-OH group.

As will be appreciated by one of skill in the art, the above list is illustrative only and by no means exhaustive, and any carbohydrate moiety may be used in compounds of the present invention that results in Flavan-3-ol glycosides with the intended therapeutic activity.

Flavan-3-ol glycosides which may be suitable for use in the present invention include, for example and without limitation, compounds according to Formula XXXIV:

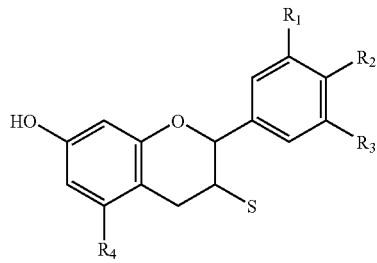

wherein each of $R_1$, $R_2$, $R_3$, and $R_4$ is as previously defined; and wherein S is as previously defined.

Moreover, as will be appreciated by one of skill in the art, the Flavan-3-ol glycosides shown herein are only exemplary of those which are known to be suitable for use, or which may be used, in the present invention, and in no way limits the scope of the present invention. Any flavan-3-ol glycoside that exhibits therapeutic activity may be used in the present invention. The suitability of a particular flavan-3-ol glycoside may be determined, for example, by bioassaying the compound according to the protocol set forth in Example 1.

For example and without limitation, additional Flavan-3-ols which may be used in compounds that exhibit therapeutic activity in the present invention include Catechin, Epicatechin and Epigallocatechin.

Also, Flavan-3-ol glycosides that may be used in compounds that exhibit therapeutic activity in the present invention may be substituted with suitable moieties in place of, or in addition to, those shown in the described compounds, so long as the flavan-3-ol glycoside exhibits therapeutic activity. Likewise, the position of the carbohydrate (S) moiety in the described compounds is exemplary only, and in no way limits the scope of the present invention. For example, the carbohydrate (S) moiety may be bound to the aglycone moiety through any suitable group thereon which permits formation of an acetal or other suitable linkage.

Anthocyanidins

Anthocyanidins have a 2-phenyl benzopyran skeleton with a positively charged oxygen molecule, and any Anthocyanidin having such a skeleton may be used as the aglycone in Anthocyanidin glycosides of the present invention that exhibits therapeutic activity, including compounds according to Formula XXXV:

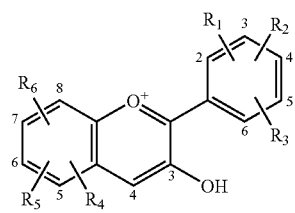

wherein each of $R_1$, $R_2$, $R_3$, $R_4$, $R_5$ and $R_6$ is independently H, OH, OCH$_3$; or a substituted or unsubstituted: alkyl; alkenyl; or alkynyl group; and wherein each of $R_1$, $R_2$, $R_3$, $R_4$, $R_5$ and $R_6$ may be substituted at any unsubstituted position on their respective ring structures.

Anthocyanidins which may be used as the aglycone in Anthocyanidin glycosides that exhibit therapeutic activity in the present invention include, for example and without limitation, compounds according to Formula XXXVI:

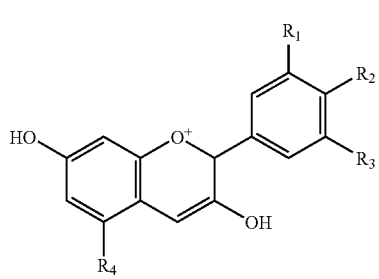

XXXVI wherein each of $R_1$, $R_2$, $R_3$, and $R_4$ is as defined previously.

Anthocyanidin glycosides which may be suitable for use in the present invention include, for example and without limitation, compounds according to Formula XXXVII:

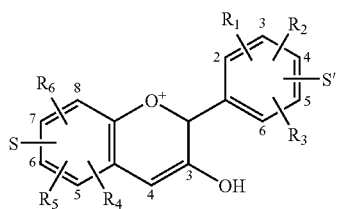

XXXVII wherein each of $R_1$, $R_2$, $R_3$, $R_4$, $R_5$ and $R_6$ is independently H, OH, $OCH_3$, or a substituted or unsubstituted: alkyl; alkenyl; or alkynyl group; and wherein each of $R_1$, $R_2$, $R_3$, $R_4$, $R_5$ and $R_6$ may be substituted at any unsubstituted position on its respective ring structure; and wherein each of S and S' is independently a carbohydrate moiety selected from, for example and without limitation, the group consisting of substituted and unsubstituted: monosaccharides, such as glucose, fructose, galactose, rhamnose, xylose or arabinose; substituted and unsubstituted disaccharides, such as sucrose, maltose, or lactose; substituted and unsubstituted trisaccharides; substituted and unsubstituted oligosaccharides; and an apiofuranosyl-glucopyranosyl moiety; and wherein at least one of S and S' is present, and the other of S and S' is optionally present; and wherein, when present, each of S and S' is bound to its respective ring structure through one of $R_1$, $R_2$, $R_3$, $R_4$, $R_5$, $R_6$, or the indicated 3-OH group.

As will be appreciated by one of skill in the art, the above list is illustrative only and by no means exhaustive, and any carbohydrate moiety may be used in compounds of the present invention that results in Anthocyanidin glycosides with the intended therapeutic activity.

Anthocyanidin glycosides which may be suitable for use in the present invention include, for example and without limitation, compounds according to Formula XXXVIII:

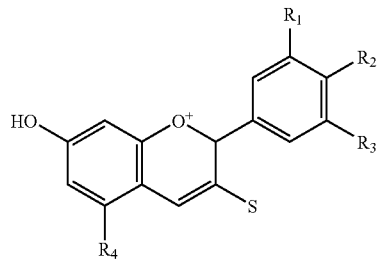

XXXVIII wherein each of $R_1$, $R_2$, $R_3$, and $R_4$ is as previously defined; and wherein S is as previously defined; and compounds according to Formula XXXIX:

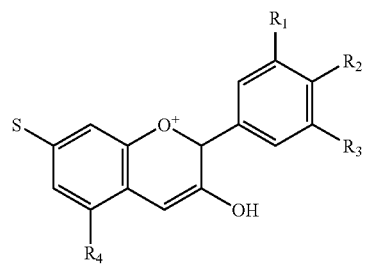

XXXIX wherein each of $R_1$, $R_2$, $R_3$, and $R_4$ is as previously defined; and wherein S is as previously defined.

Moreover, as will be appreciated by one of skill in the art, the Anthocyanidin glycosides shown herein are only exemplary of those which are known to be suitable for use, or which may be used, in the present invention, and in no way limits the scope of the present invention. Any Anthocyanidin glycoside that exhibits therapeutic activity may be used in the present invention. The suitability of a particular Anthocyanidin glycoside may be determined, for example, by bioassaying the compound according to the protocol set forth in Example 1.

For example and without limitation, additional Anthocyanidins which may be used as the aglycone in Anthocyanidin glycosides that exhibit therapeutic activity in the present invention that exhibits therapeutic activity include Cyanidin, Delphinidin, Malvidin, Pelargonidin, Peonidin, and Petunidin.

Also, Anthocyanidin glycosides that exhibit therapeutic activity and may be used in the present invention may be substituted with suitable moieties in place of, or in addition to, those shown in the described compounds, so long as the Anthocyanidin glycoside exhibits therapeutic activity. Likewise, the position of the carbohydrate (S) moiety in the described compounds is exemplary only, and in no way limits the scope of the present invention. For example, the carbohydrate (S) moiety may be bound to the aglycone moiety through any suitable group thereon which permits formation of an acetal or other suitable linkage.

As used in the present invention without limitation, the term "prodrug" is given its conventional and generally art-recognized definition as a compound that is provided to a patient in a generally inactive form (or in a form with substantially reduced activity), and which is converted into an active drug in vivo, such as through enzymatic cleavage. For example, upon hydrolysis by enzymes such as pancreatic or salivary disaccharides or by conditions in the stomach or other locations in vivo, a compound according to Formula IV with, for example, two glucose moieties may yield a compound with, for example, one glucose moiety. Generally, the resulting active drug is generally referred to as a "metabolite" of the prodrug. In the present invention, certain prodrugs may, for example, independently meet the limitations of a given formula, while other prodrugs meet the limitations of such formula only after conversion into their active form.

As used in the present invention, to state that a composition "includes a compound according to (or of) a particular formula, or a pharmaceutically-acceptable salt, enantiomer, diasteriomer, racemic mixture, enantiomerically-enriched mixture, solvate, or prodrug of such formula", specifically means that such composition may include either a single compound falling within such definition, or may include more than one compound falling within such definition. For example, a pharmaceutical composition of the present invention that includes a "therapeutically effective amount of a compound according to Formula IV, or a pharmaceutically-acceptable salt, enantiomer, diasteriomer, racemic mixture, enantiomerically-enriched mixture, solvate, or prodrug of Formula IV" may include a single compound according to Formula IV, or may include one compound that meets the above definition in combination with another combination that also meets the above definition. As will be appreciated by one of skill in the art, pharmaceutical compositions of the present invention may include any number of compounds in combination that fall within the provided definitions, so long as they are therapeutically or otherwise useful as intended.

Pharmaceutical compositions of the present invention generally include, for example and without limitation, therapeutically effective amounts of compounds according to Formulas IV, XIII, XIX, XXVII, XXXIII, and XXXVII, or a pharmaceutically-acceptable salt, enantiomer, diasteriomer, solvate, or prodrug of compounds according to such Formulas, in a pharmaceutically effective carrier. As used in the present invention, the term "pharmaceutically acceptable salts" refers to salts prepared, for example and without limitation, from pharmaceutically acceptable non-toxic bases including inorganic bases and organic bases. Salts derived from inorganic bases include, for example, aluminum, ammonium, calcium, copper, ferric, ferrous, lithium, magnesium, manganic salts, manganous, potassium, sodium, zinc, and the like. Salts derived from pharmaceutically acceptable organic non-toxic bases include, for example, salts of primary, secondary, and tertiary amines, substituted amines including naturally occurring substituted amines, cyclic amines, and basic ion exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Pharmaceutical compositions including a compound according to Formula IV, such as a compound of Formula X, or a pharmaceutically-acceptable salt, enantiomer, diasteriomer, solvate, or prodrug thereof, in a pharmaceutically effective carrier, are useful, for example and without limitation, for the relief of pain, fever and inflammation of a variety of conditions, including rheumatic fever; symptoms associated with influenza or other viral infections; common cold; low back and neck pain; dysmenorrhea; headache; toothache; sprains and strains; myositis; neuralgia; synovitis; arthritis, including rheumatoid arthritis and degenerative joint diseases (e.g., osteoarthritis); gout and ankylosing spondylitis; bursitis; burns; injuries; and pain and inflammation following surgical and dental procedures, as illustrated and suggested by the present Examples. In addition, compositions and compounds of the present invention may inhibit cellular neoplastic transformations and metastic tumor growth, and hence may be useful in the treatment of cancer.

Moreover, pharmaceutical compositions including a compound according to Formula IV, such as a compound of Formula X, or a pharmaceutically-acceptable salt, enantiomer, diasteriomer, solvate, or prodrug thereof, are expected to be useful in therapeutic combinations with known therapeutic compounds, for example analgesics. For example, analgesics expected to have therapeutic utility in combination with compounds of the present invention include, but are not limited to, NSAIDS such as the salicylates; acetaminophen; ibuprofen; and COX-2 inhibitors.

Pharmaceutical compositions including compounds according to Formula IV, such as a compound of Formula X, or pharmaceutically-acceptable salts, enantiomers, diasteriomers, solvates, or prodrugs of Formula X, may be administered to a patient in need thereof in any acceptable form in dosage unit formulations that employ conventional non-toxic pharmaceutically acceptable carriers, adjuvants and vehicles that permit such compositions of the present invention to have therapeutic activity. For example, such compositions may be in an orally-administrable form; a topical form; may be administered to the sinuses, throat or lungs; or may be administered parenterally.

Pharmaceutical compositions of the present invention that are intended for oral use may be in the form of a pill, tablet, gelcap, or hard or soft capsule (each of which may be in an immediate, sustained or time-release formulation); lozenge; throat spray; solution; emulsion; cream; paste; gel; cough drop; dissolvable strip; lollipop; gum; aqueous or oily suspension, dispersible powder/granules; syrup; elixir; and may be prepared according to any method known in the art for the manufacture of pharmaceutical compositions. Such compositions may further contain one or more agents selected from the group consisting of sweetening agents, flavoring agents, coloring agents and preserving agents in order to provide pharmaceutically elegant and palatable preparations. By dissolvable strip is meant a sheet of material that can be placed in the mouth to dissolve and release the active ingredient or prodrug. Such dissolvable strips are also known as flavor strips or oral care strips. Dissolvable strips are often carbohydrate-based. Tablets typically contain the active ingredient or prodrug in admixture with non-toxic pharmaceutically acceptable excipients which are suitable for the manufacture of such tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example, magnesium stearate, stearic acid or talc. Tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

With respect to capsules, in hard gelatin capsule formulations the active ingredient(s) or prodrug may be mixed with an inert solid diluent, for example, calcium carbonate, calcium phosphate or kaolin; and in soft gelatin capsule formulations the active ingredient(s) or prodrug may be mixed with water or an oil medium, for example peanut oil, liquid paraffin, or olive oil.

Aqueous suspensions typically contain the active material in admixture with excipients suitable for the manufacture of such aqueous suspensions. Such excipients may be suspending agents, for example sodium carboxymethylcellulose, methylcellulose, hydroxy-propylmethycellulose, sodium alginate, polyvinyl-pyrrolidone, gum tragacanth and gum acacia; dispersing or wetting agents, such as a naturally-occurring phosphatide (e.g., lecithin), condensation products of an alkylene oxide with fatty acids (e.g., polyoxyethylene stearate), condensation products of ethylene oxide with long chain aliphatic alcohols (e.g., heptadecaethylene-oxycetanol), condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyethylene sorbitan monooleate). The aqueous suspensions may also contain one or more preservatives, for example ethyl, n-propyl, or p-hydroxybenzoate; one or more coloring agents; one or more flavoring agents; and/or one or more sweetening agents, such as sucrose, saccharin or aspartame.

Oily suspensions may be formulated by suspending the active ingredient or prodrug in a vegetable oil, such as arachis oil, olive oil, sesame oil or coconut oil; or in mineral oil, such as liquid paraffin. Such oily suspensions may also contain a thickening agent, such as beeswax, hard paraffin or cetyl alcohol. Sweetening agents, such as those set forth above, and flavoring agents, may also be added to provide a palatable oral preparation. Such compositions may be preserved by the addition of an anti-oxidant, such as ascorbic acid.

Dispersible powders and granules suitable for preparation of an aqueous suspension by the addition of water typically provide the active ingredient or prodrug in admixture with a dispersing or wetting agent, a suspending agent and one or more preservatives. Suitable dispersing or wetting agents and suspending agents are exemplified by those aforementioned. Additional excipients, for example sweetening, flavoring and coloring agents, may also be present.

Pharmaceutical compositions of the present invention may also be in the form of oil-in-water emulsions. In such preparations, the oily phase may be a vegetable oil (e.g., olive oil or arachis oil), a mineral oil (e.g., liquid paraffin), or mixtures of such vegetable and mineral oils. Suitable emulsifying agents may be naturally-occurring phosphatides, such as soy bean, lecithin, esters or partial esters derived from fatty acids and hexitol anhydrides (e.g., sorbitan monooleate), and condensation products of such partial esters with ethylene oxide (e.g., polyoxyethylene sorbitan monooleate). Such emulsions may also contain sweetening and flavoring agents.

Syrups and elixirs may be formulated with sweetening agents, such as glycerol, propylene glycol, sorbitol or sucrose. Such formulations may also contain a demulcent, a preservative, and flavoring and/or coloring agents. Pharmaceutical compositions of the present invention may also be in the form of a sterile injectable aqueous or oleaginous suspension, which may be formulated according to methods known in the art using, for example, suitable aforementioned dispersing or wetting agents, and suspending agents. Such a sterile injectable preparation may also be a sterile injectable solution or suspension in a non-toxic parenterally-acceptable diluent or solvent, such as a solution in 1,3-butane diol. Acceptable vehicles and solvents that may be employed include, for example, water, Ringer's solution and isotonic sodium chloride solution. Additionally, sterile, fixed oils may be employed as a solvent or suspending medium, such as a bland fixed oil, including synthetic mono- or diglycerides. Fatty acids such as oleic acid, may also be used in the preparation of injectables.

As aforementioned, the inventive compounds and pharmaceutical compositions may be administered in a controlled or sustained release system. Such systems include, for example, the use of a pump (see, for example, Langer and Sefton, (1987) CRC *Crit. Ref. Biomed.* 14:201; Buchwald et al. (1980), *Surgery* 88:507; Saudek et al. (1989), *N. Engl. J. Med.* 321:574), and more typically (with respect to oral formulations such as pills, tablets, etc.), the use of polymeric materials (see, for example, *Medical Applications of Controlled Release*, Langer and Wise (eds.) (1974), CRC Pres., Boca Raton, Fla.; *Controlled Drug Bioavailability, Drug Product Design and Performance*, Smolen and Ball (eds.) (1984), Wiley, New York; Ranger and Peppas, J. (1983), *Macromol. Sci. Rev. Macromol. Chem.* 23:61; Levy et al. (1985), *Science* 228:190; During et al. (1989), *Ann. Neurol.* 25:351; Howard et al. (1989), *J. Neurosurg.* 71:105). Other means of effecting controlled release involve, for example, placing the therapeutic composition in proximity of the therapeutic target, thus requiring only a fraction of the systemic dose (see, for example, Goodson, *Medical Applications of Controlled Release*, (1984) vol. 2, pp. 115-138). Other controlled release systems which may be employed include those reviewed by Langer (*Science* (1990) 249:1527-1533).

Pharmaceutical compositions including compounds of Formula IV, or pharmaceutically-acceptable salts, enantiomers, diastereomers, racemic mixtures, enantiomerically-enriched mixtures, solvates, or prodrugs of Formula X, may also be administered in the form of rectal suppositories. Such compositions may be prepared by mixing the active compound with a suitable non-irritating excipient which is solid at ordinary temperatures but liquid at rectal temperature, and will therefore melt in the rectum to release the active compound. Suitable rectal suppository materials include cocoa butter and polyethylene glycols.

For topical administration of the inventive compositions and compounds, a liquid solution; liquid spray; emulsion; cream; paste; gel; lotion; foam; impregnated dressing; ointment; jelly; or mouth wash/gargle may be employed.

Pharmaceutical compositions and compounds of the present invention may also be administered occularly, such as in the form of eye-drops, ointments, sprays or conjunctival timed-release inserts. Administration of the inventive pharmaceutical compositions to the sinuses, throat, or lungs may be in the form of inhalable particles, inhalable solution, droplets, inhalation sprays, or aerosol. Further, such compositions may be administered parenterally, such as by subcutaneous injection, intravenously, intramuscularly, intrasternally, or by various infusion techniques.

Pharmaceutical compositions of the present invention include, for example and without limitation, analgesically-effective amounts of compounds according to Formulas IV, XIII, XIX, XXVII, XXXIII, and XXXVII, and pharmaceutically-acceptable salts, enantiomers, diastereomers, racemic mixtures, enantiomerically-enriched mixtures, solvates, or prodrugs of compounds according to such Formulas, and may contain between about 0.01 mg to about 500 mg per unit dose of such compounds. In one embodiment, the amount is between about 1 mg to about 100 mg per unit dose.

The dosage regimen for pharmaceutical compositions of the present invention will, of course, vary depending upon known factors, such as the pharmacodynamic characteristics of the particular agent and its mode and route of administration; the species, age, sex, general health, medical condition, diet, and body weight of the recipient; the nature and extent of the symptoms; the kind of concurrent treatment; the frequency of treatment; the time of administration; route of administration, the renal and hepatic function of the patient, and the effect desired. A physician (or veterinarian in such case as the inventive compositions are use in the treatment of non-human animals) can determine and prescribe the effective amount of the drug required to prevent, counter, or arrest the progress of the disease state.

Moreover, the amount of active ingredient or prodrug that may be combined with carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient or prodrug, typically 25 mg, 50 mg, 100 mg, 200 mg, 300 mg, 400 mg, 500 mg, 600 mg, 800 mg, or 1000 mg.

Once formulated, pharmaceutical compositions of the present invention may be used without limitation for various therapeutic uses, including analgesia. For examples, such compositions may be used to treat pain and/or discomfort by administration to an individual experiencing pain or discomfort. In one embodiment, compositions according to the present invention are administered to treat one or more symptoms of a cold or flu. Such symptoms include sore throat, eyes, ears, or sinuses. Alternatively, such compositions may be used to treat pain due to abrasions, rash, or minor cuts or burns. For example, in one embodiment, compositions of the present invention are impregnated in adhesive bandages to provide relief from the discomfort of sores or blisters. In another embodiment, compositions of the present invention are applied topically or intramuscularly to provide relief from muscular or joint pain, or relief from neuropathy. Administration routes also include time-released formulations to provide extended or long-range treatment.

Moreover, compounds according to Formula IV, such as a compound of Formula X, or pharmaceutically-acceptable salts, enantiomers, diasteriomers, racemic mixtures, enantiomerically-enriched mixtures, solvates, or prodrug thereof, may be entirely natural in origin, or entirely synthetic, or a modified form of a naturally-occurring compound (i.e. semi-synthetic).

Where a compound of Formula IV, such as a compound of Formula X, or a pharmaceutically-acceptable salt, enantiomer, diasteriomer, racemic mixture, enantiomerically-enriched mixture, solvate, or prodrug thereof, is natural in origin, it is generally necessary to substantially purify and isolate such compound from the cellular debris of the organism that produced the compound. In this regard, in one embodiment, sweet green bell peppers (*Capsicum anuum ssp. grossum*) are sliced and pureed by hand or by mechanical means. The stems and/or seeds may be removed prior to the preparation of the puree. The puree may be filtered to a juice by conventional methodology, including, but not limited to, vacuum filtration. Highly non-polar compounds including, but not limited to chlorophylls and waxes may be removed from the juice by partitioning the juice between the hydrophilic aqueous phase and a non-polar solvent including, but not limited to, diethyl ether. The aqueous phase may be utilized for further separation, utilized as is, or subjected to trituration with short chain alcohols including, but not limited to methanol or ethanol to precipitate out compounds including, but not limited to, polypeptides and long chain carbohydrates.

The juice and/or triturated supernatant may be concentrated by conventional methodology such as rotary evaporation or freeze-drying or may be directly separated by column chromatography with sorbents (stationary phase) including, but not limited to, C-18 with fractions eluted with a gradient solvent (mobile phase) system including, but not limited to water:methanol and/or Sephadex LH-20 eluted with small chain alcohols including, but not limited to, pure methanol. Sub-fractions containing active analgesic compounds can be purified by methods including, but not limited to, HPLC or HPLC/mass spectrometry to yield pure isolates of active compounds.

Turning now to the following non-limiting Examples, the isolation, identification, and therapeutic effectiveness of compositions and compounds of the present invention are shown.

EXAMPLE 1

Analgesic Bioassay Protocol

A rat hindpaw assay was used to determine the therapeutic effectiveness of various extracts/compounds as analgesics in the present invention.

Sprague-Dawley rats (225-250 g, male) were anesthetized with urethane and placed on their sides on a disposable Chux pad. Both hindpaws for each rat were blackened with India ink which was allowed to dry for 10 minutes. An ELH projector lamp calibrated to a standard mW/cm was used as a pain stimulus and was condensed into an area of 5×15 mm on each hindpaw and placed perpendicular to, and 72 mm from, each hindpaw.

Multiple baseline hindpaw withdrawal latency times were recorded (in seconds) for each medial and each lateral surface of each hindpaw. Subsequently, 100 µl of 1 µmolar capsaicin was applied with a pipette to cover one hindpaw of each animal and allowed to dry for 10 minutes, rendering the capsaicin-treated hindpaw hypersensitive to pain stimulus relative to the non-capsaicin treated hindpaw (and thereby decreasing the withdrawal latency period for the capsaicin-treated hindpaw relative to the non-treated hindpaw).

Both hindpaws were then re-blackened with India ink which was allowed to dry for 10 minutes, and hindpaw withdrawal latencies were recorded for both the capsaicin-treated and untreated hindpaws on both the medial and lateral aspects of both hindpaws at 20, 25 and 30 minutes. A significant drop in the withdrawal latency period was seen with the capsaicin-treated hindpaw, consistent with the reported effects of capsaicin as a pain hyper-sensitizing agent at general concentrations and dosages used in this bioassay. By contrast, only minor drops in the withdrawal latency periods of the untreated hindpaws was seen, and the effect that was observed is believed to be due to the central mechanism effect of capsaicin-treatment on the other hindpaw.

To determine the analgesic properties of each fraction, 100 µl of each fraction were applied to the capsaicin-treated hindpaw by pipette and permitted to dry (the untreated hindpaw was not treated with the fraction). Hindpaw withdrawal latencies were then recorded at 5, 20 and 30 minutes for both the capsaicin/fraction-treated hindpaw and the untreated hindpaw. An increase in the hindpaw withdrawal time was indicative of an analgesic effect by the applied fraction.

EXAMPLE 2

Isolation of Analgesic Compounds

Twelve (12) sweet green bell peppers (*Capsicum anuum* ssp. *grossum*) with stems, seeds and septae removed were put through a juice extractor (Panasonic model #MJ66PR) to yield 1200 ml liters of unfiltered juice. The juice was suction filtered with coarse filter paper through a Buchner funnel to yield 1.0 liters of filtered green pepper juice.

500 ml of filtered juice was partitioned with 500 ml of diethyl ether to remove waxes and chlorophylls. This partitioning was performed for a total of three times. Three layers were separated, the aqueous layer, the ether layer and an intermediate flocculent layer. Aliquots of each layer were tested by the Analgesic Bioassay (Example 1). Only the aqueous layer exhibited analgesic activity.

The aqueous layer was rotary evaporated at room temperature to 10 ml of a light brown gel which was triturated with two successive volumes of 100 ml methanol at room temperature to precipitate out long chain carbohydrates and polypeptides. The methanolic suspension was suction filtered with a Buchner funnel. The clear filtrate was dried down to 1 ml of a viscous amber liquid in a rotary evaporator at 40° C.

1.0 g of the concentrated methanolic extract was fractionated by column chromatography with a stationary phase of C-18 reverse phase silica gel (Sep-Pak 35 cc C-18 10 g, Waters, Chicago, Ill.). 20 ml fractions were eluted with a gravity-fed, gradient solvent system of 0:1 to 1:0 methanol/water (mobile phase) in increments of 20% methanol per step.

Aliquots of each fraction tested by the Analgesic Bioassay (Example 1) demonstrated analgesic activity concentrated in fraction E (the 80% methanol:water fraction). Bioassay testing further demonstrated retention of bioactivity on heating of active samples to 45° C. and on acidifying the same sample to pH 4.4. Analgesic activity was lost on alkalinization to pH 8.4. The analgesic effect of analgesic fractions was not lost on administration of naloxone, a narcotic antagonist, to the test animals, which was indicative that the induced analgesia was not from a narcotic entity (Table 1). Fraction E showed increasing analgesic effect over time even after naloxone administration.

TABLE 1

Analgesic Effect of Extract Fraction E

| Fraction | n | Avg. Baseline | Avg. Post-Cap | Avg. Post-Fract | Avg. Post-Naloxone |
|---|---|---|---|---|---|
| E (80% MeOH) | 2 | 12.65 | 5.38 | 18.05 | 15.36 |
| SEM | | 0.48 | 0.42 | 4.02 | 0.82 |
| Control | 2 | 12.58 | 10.09 | 10.41 | N/A |
| SEM | | 0.32 | 0.34 | 1.84 | N/A |

EXAMPLE 3

Sub-fractionation of Fraction E 1.0 g of the original concentrated methanolic extract was fractionated by column chromatography with a stationary phase of C-18 reverse phase silica gel (Sep-Pak 35 cc C-18 10 g, Waters, Chicago, Ill.). 20 ml fractions were eluted with a gravity-fed, gradient solvent system of 0:1 to 1:0 methanol/water (mobile phase) in increments of 20% methanol per step.

1.0 g of the concentrated 80% methanol fraction was re-fractionated by column chromatography with a stationary phase of C-18 reverse phase silica gel (Sep-Pak 35 cc C-18 10 g, Waters, Chicago, Ill.). 20 ml fractions were eluted with a gravity-fed, gradient solvent system of 0:1 to 1:0 methanol/water (mobile phase) in increments of 20% methanol per step. The 80% methanol fractions were collected in 5 ml aliquots labeled EEa, EEb, EEc and EEd. All of these sub-fractions exhibited analgesic activity with the greatest analgesic activity noted in fraction EEa.

EXAMPLE 4

Identification of Sub-fraction BMBW-M40i 3000 mL of the juice of sweet green bell peppers (*Capsicum anuum* ssp. *grossum*) exhibiting strong analgesic activity by the "analgesic bioassay protocol" (Example 1) was partitioned with 1000 ml of diethyl ether. This partitioning was performed for a total of three times. The aqueous layer was filtered, concentrated and lyophilized in vacuo at 35.8° C. to yield 135.2 g of brown extract.

21.0 g of the lyophilized extract was fractionated by column chromatography with a stationary phase of C-18 reverse phase silica gel (40 µm; J. T. Baker, Phillipsburg, N.J.). Fractions were eluted with a gradient solvent system of 0:1 to 1:0 methanol/water (mobile phase) in increments of 10% methanol per step. Thirteen fractions were obtained and compared by thin layer chromatography to known bioactive fraction EEa (see Example 3).

Bioassays were performed as described above on fractions eluted with 30%-80% methanol based on matching thin layer chromatograms to standard EEa. Fractions adjacent to these matching fractions were also bioassayed. Results of bioassay testing (latencies in seconds and corresponding standard errors of the mean (SEM) were recorded for fractions obtained throughout the isolation and purification procedures described. Sub-fractionations were guided by both 1) bioassay testing, as described above, and 2) comparing thin layer chromatograms of fractions and sub-fractions obtained as described herein to fraction EEa (see Example 3). Based on bioassayed analgesic activity, aliquots of the 40% fraction (BMBW-M40, total weight 99.8 mg) and the 60% fraction (BMBW-M60, total weight 102.1 mg) were further sub-fractionated.

66.0 mg of BMBW-M40 was sub-fractionated by column chromatography with a stationary phase of Sephadex LH-20 (10.0 g, 25-100 µm; Pharmacia Fine Chemicals, Piscataway, N.J.). Sub-fractions were eluted with a solvent system of pure methanol. Sub-fractions were combined based on HPLC analyses to yield twelve sub-fractions.

Bioassays were performed as described above on all twelve fractions. Based on its assayed bioactivity, fraction BMBW-M40i (total weight 3.6 mg) was further sub-sub-fractionated.

70.5 mg of BMBW-M60 was sub-fractionated by column chromatography with a stationary phase of Sephadex LH-20 (10.0 g, 25-100 µm; Pharmacia Fine Chemicals, Piscataway, N.J.). Sub-fractions were eluted with a solvent system of pure methanol. Sub-fractions were combined based on HPLC analyses to yield sixteen sub-fractions. In bioassays performed as described above, all of the BMBW-M60 sub-fractions failed to demonstrate the significant retention of analgesic activity.

Sub-fraction BMBW-M40i was analyzed by HPLC analyses on a Waters 2690 separation module equipped with a Waters 996 photodiode array detector and Empower software using a Phenomenex Aqua $C_{18}$ column (4.6×250 mm, 5 µm) and a HPLC gradient program (Table 2), column at room temperature, 65 min run time.

TABLE 2

HPLC Analysis of Sub-fraction BMBW-M40i

| Time (min) | Flow (ml/min) | Water (%) | Methanol (%) | Curve |
|---|---|---|---|---|
| 0.00 | 1.00 | 95.0 | 5.0 | Linear-6 |
| 10.00 | 1.00 | 50.0 | 50.0 | Linear-6 |
| 15.00 | 1.00 | 50.0 | 50.0 | Linear-6 |
| 50.00 | 1.00 | 5.0 | 95.0 | Linear-5 |
| 65.00 | 1.00 | 95.0 | 5.0 | Linear-6 |

Nine peaks were identified and labeled BMBW-M40i1,2,3,4,A,5,B,6,7 and a broad bimodal peak between 45 and 55 minutes labeled 8 and 9 (see FIG. 1, which shows HPLC chromatograms and UV spectra of BMBW-M40i peaks). The UV spectra in FIG. 1 indicated that peaks 1, 2, 3, 4 and 7 were likely to have aromatic rings and peaks A, B, 5, and 6 were unlikely to have aromatic rings.

Figure 2:
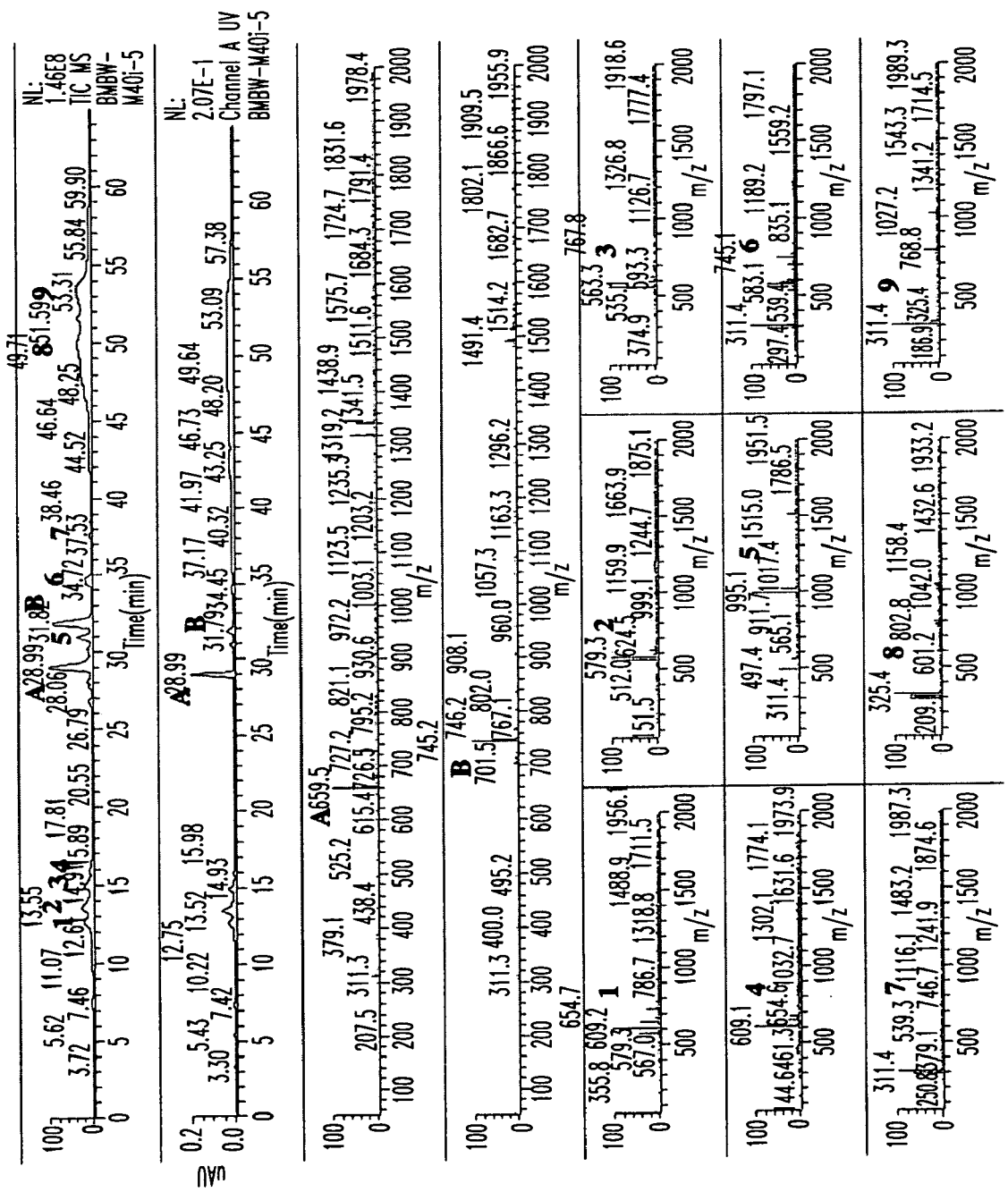
FIG. 2: TIC, UV (221 nm) and negative ESIMS spectra of the peaks of BMBW-M40i from Example 4.
Figure 3:
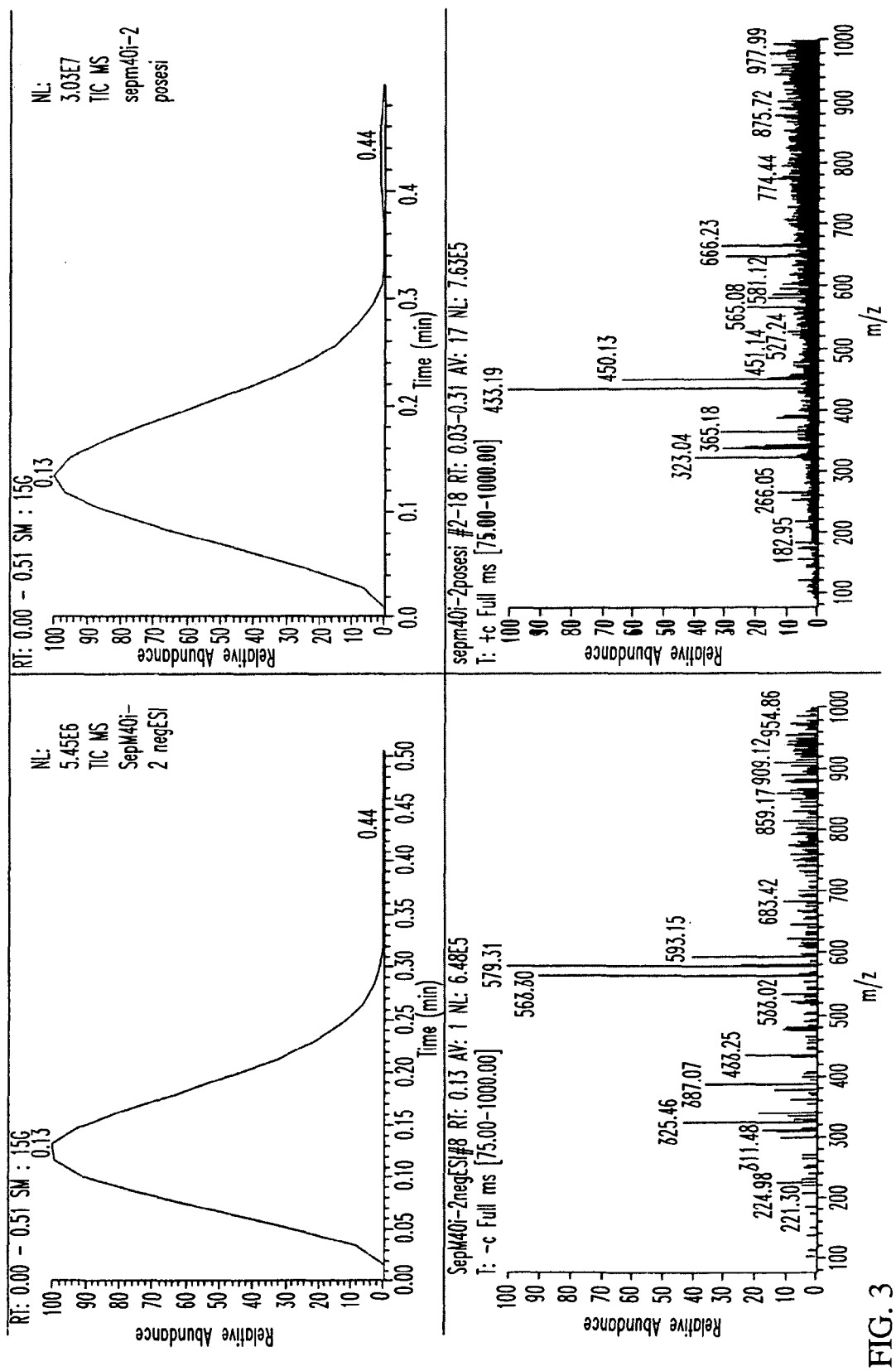
FIG. 3: ESIMS of BMBW-M40i-2 from Example 4.

Sub-fraction BMBW-M40i was subjected to HPLC-MS analysis. 1.8 mg of BMBW-M40i was dissolved in 1.0 ml methanol. 20 µL of this solution was diluted with 100 µL of methanol and was analyzed by negative ESIMS with a ThermoFinnigan LCQ instrument (San Jose, Calif.) equipped with Xcalibur software. The sample was introduced by a Waters 2690 separation module, equipped with a Waters 2487 dual X absorbance detector. The capillary voltage was set at 10 V with a spray voltage of 4.5 kV, tube lens offset of 0 V and capillary temperature of 230° C. The sheath gas and auxiliary gas were both Nitrogen with flow rates of 80 and 30, respectively. Results of this negative ESIMS are shown in FIG. 2.

HPLC/MS by positive ESIMS was performed on BMBW-M40i on an Agilent Technologies 1100 Series LC/MSD model G1946D using electrospray ionization. Ionization was carried out with a drying gas temperature of 200° C., a nebulizer pressure of 40 psi and a flow rate of 13 L/min. The mass range scanned was between 140 and 1500 amu with fragmentor values of 70 volts in both positive and negative mode. The capillary was set to 4000 volts. Prior to mass spectral analysis the sample was analyzed on an Agilent Technologies 1100 analytical HPLC using a Zorbax Eclipse XDB-C18 2.1 mm×150 mm 5-micron column (part number 993700-902) operated at a temperature of 36° C. The mobile phase consisted of 0.1% (v/v) formic acid and 50 uM ammonium acetate in water (Eluent A) and of 0.1% (v/v) formic acid and 50 uM ammonium acetate in acetonitrile (Eluent B) according to the gradient in Table 3.

TABLE 3

HPLC Analysis of Sub-fraction BMBW-M40i

| Time (min) | Flow (ml/min) | Eluent A (%) | Eluent B (%) | Curve |
|---|---|---|---|---|
| 0.00 | 0.4 | 90.0 | 10.0 | Linear |
| 2.00 | 0.4 | 90.0 | 10.0 | Linear |
| 60.00 | 0.4 | 55.0 | 45.0 | Linear |
| 80.00 | 0.4 | 0.0 | 100.0 | Linear |
| 85.00 | 0.4 | 0.0 | 100.0 | Linear |

The injection volume was 25 µL. Simultaneous monitoring was performed at 230 nm and 260 nm. Spectra were recorded from 200 to 900 nm. Data was processed using Agilent's Chemstation software. Mass spectral data by negative ESIMS revealed a minor constituent of BMBW-M40i to have m/z 579 (M-H+).

1.6 mg of BMBW-M40i was sub-sub-fractionated by analytic HPLC on a Waters 690 separation module equipped with a Waters 996 photodiode array detector and Empower software using a 250×4.6 mm i.d., 5 µm, Aqua $C_{18}$ column (Phenomenex, Torrance, Calif.). An HPLC gradient program (see Table 1) resulted in ten sub-sub-fractions, BMBW-M40i-1,2,3,4,A,5,B,6,7 and 8, which were all subjected to bioassay. Results from various fractions: BMBW-M40i-2 ("Fraction i2") and the inactive fraction: BMBW-M40i-B ("Fraction iB") are summarized in Table 4. Latencies are recorded in seconds along with their corresponding standard errors of the mean (SEM).

TABLE 4

Analgesic Bioassay Results: Sub-fractions i2 and iB

| Fraction | n | Avg Baseline | Avg Cap20 | Avg Cap 25 | Avg Cap 30 | Avg All Cap | Avg Ext 5 | Avg Ext 20 | Avg Ext 30 |
|---|---|---|---|---|---|---|---|---|---|
| Frac i2 580 (0.08 mg) | 5 | 13.97667 | 7.33 | 7.03 | 6.56 | 6.973333 | 19.42 | 11.9 | 8.7 |
| SEM | | 0.719673 | 1.316038 | 0.250355 | 0.30485 | 0.316879 | 0.432512 | 1.726332 | 1.423376 |
| Control | 5 | 12.60667 | 11.42 | 12.03 | 11.43 | 11.62667 | 13.21 | 12.05 | 12.68 |
| SEM | | 0.719673 | 1.316038 | 1.279935 | 0.72081 | 0.636548 | 1.126198 | 1.171443 | 0.83264 |
| Frac iB 746 (0.13 mg) | 5 | 10.63333 | 9.47 | 7.84 | 7.32 | 8.21 | 12.22 | 6.79 | 7.98 |
| SEM | | 0.738914 | 1.441762 | 0.844748 | 0.570341 | 0.592818 | 1.678346 | 0.860032 | 0.810871 |
| Control | 5 | 12.75 | 12.63 | 12.14 | 13.81 | 12.86 | 12.07 | 13.04 | 12.76 |
| SEM | | 0.738914 | 1.056625 | 1.171912 | 1.319802 | 0.674317 | 1.151719 | 1.278384 | 1.267473 |

Latencies after application of Fraction i2 at 20 minutes as compared to the 30 minute capsaicin latencies were highly statistically significant (by single factor ANOVA) with a of P-value of 0.00695081. The results with Fraction iB were not statistically significant with a P-value of 0.613788806.

Sub-sub-fraction BMBW-M40i-2 (FIG. 5) was tested by both negative and positive ESIMS by direct injection. Samples were dissolved in MeOH and were introduced by a Waters 2690 separations module using an isocratic solvent system of 50:50 MeCN/$H_2O$, a flow rate of 0.3 ml/min. The capillary voltage was 10 V, the spray voltage was 4.5 kV, and the tube lens offset was 0 V. The capillary temperature was 230° C. The sheath gas and auxiliary gas were both nitrogen with flow rates of 80 and 30, respectively.

Figure 7:
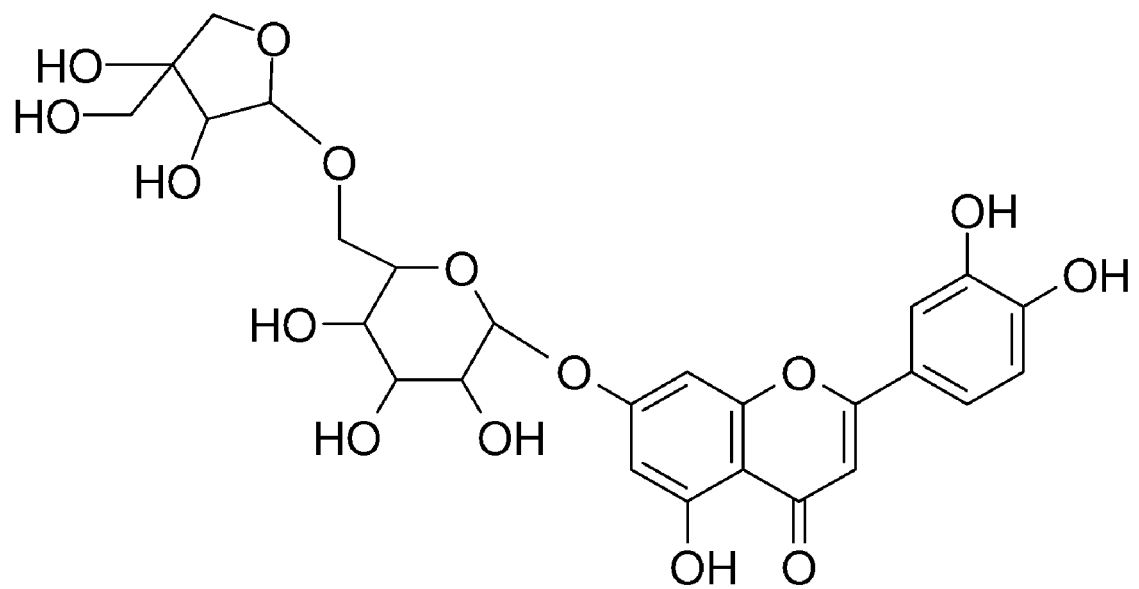
FIG. 7: 2-D structure of Compound-580 (Formula X).
Figure 8:
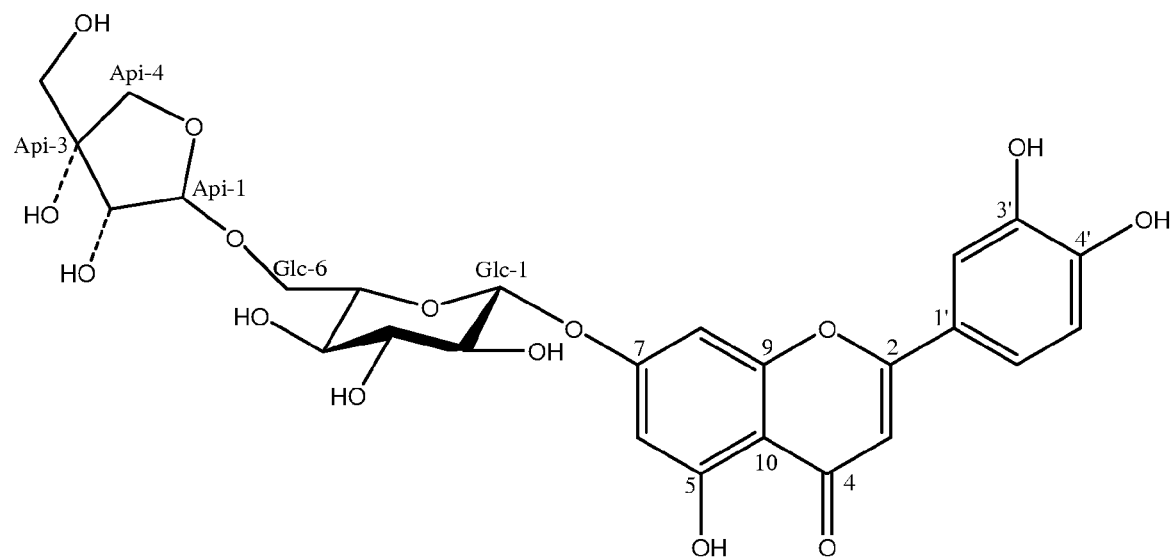
FIG. 8: Detailed structure of Compound-580 (Formula $X_1$).

Sub-sub-fraction BMBW-M40i-2 consisted primarily of negative ESIMS m/z 579.3 ("Compound 580"; Formula X in FIG. 7; Formula $X_1$ in FIG. 8). Negative ESIMS m/z 745.14, was the primary constituent of BMBW-M40i-B, which had been shown to have no analgesic activity by bioassay with the Analgesic Bioassay Protocol (Example 1).

Figure 4:
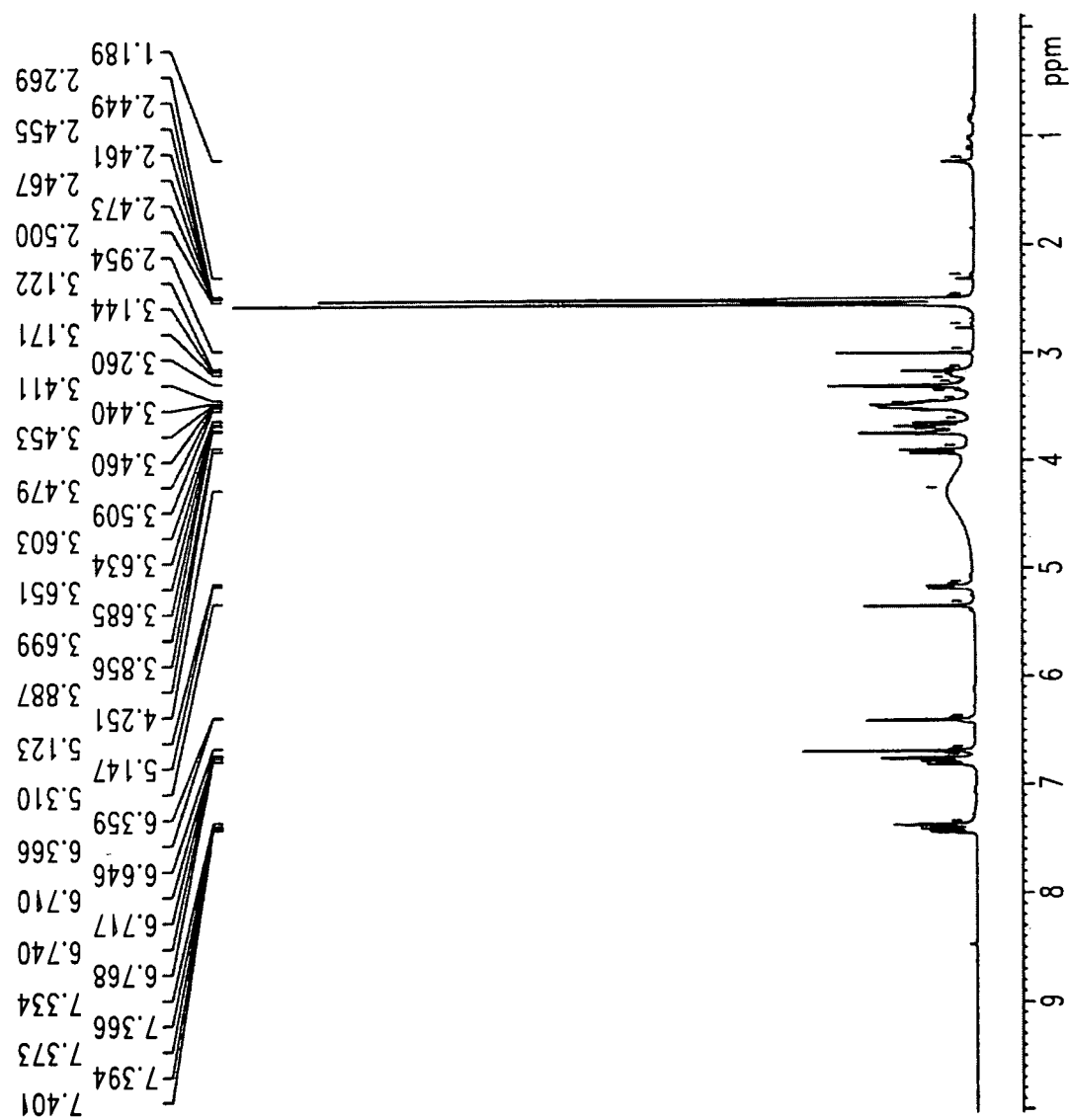
FIG. 4: 1D $^1$H-NMR spectra of Compound-580 from Example 4.
Figure 5:
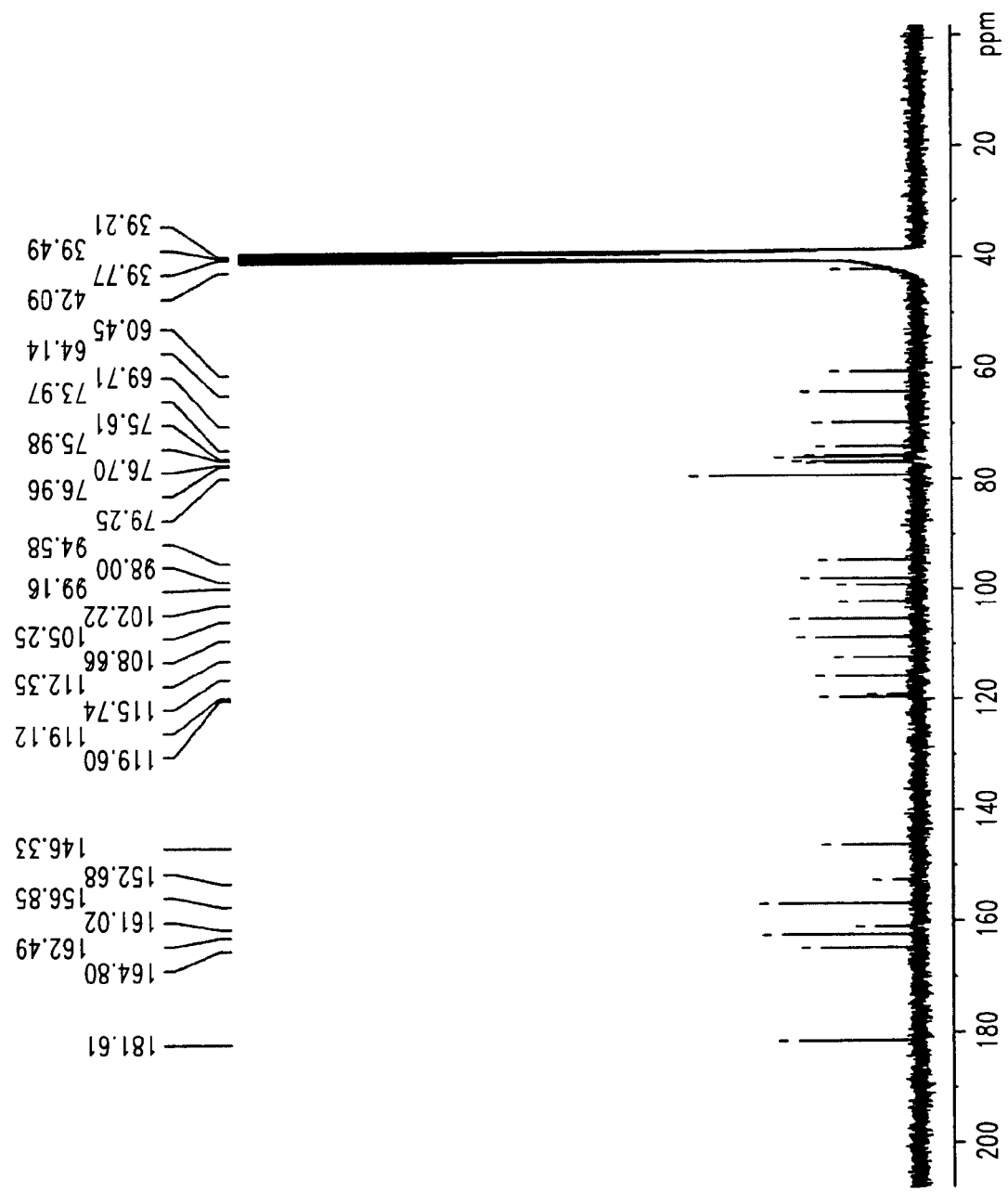
FIG. 5: 1D $^{13}$C NMR spectra of Compound-580 from Example 4.
Figure 6:
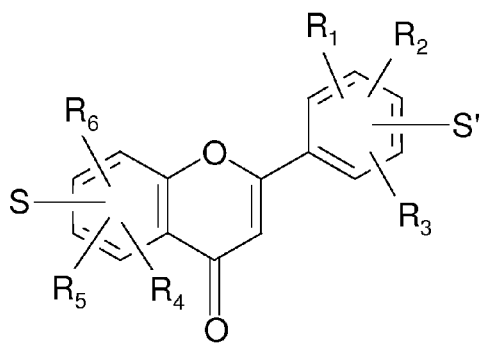
FIG. 6: Structure of generic flavonoid glycosides (Formulas IV, XIII, XIX, XXVII, XXXIII, and XXXVII) which may be used in the present invention.
Figure 6:
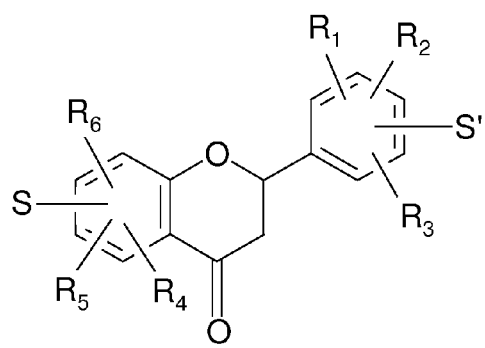
Figure 6:
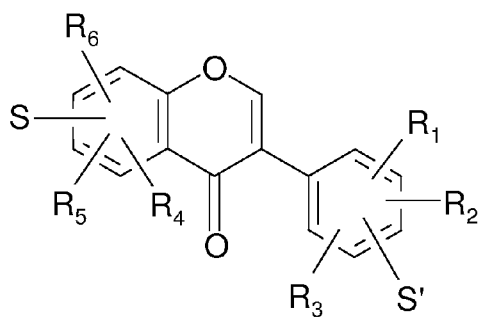
Figure 6:
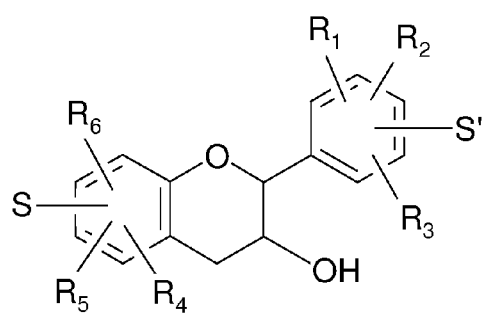
Figure 6:
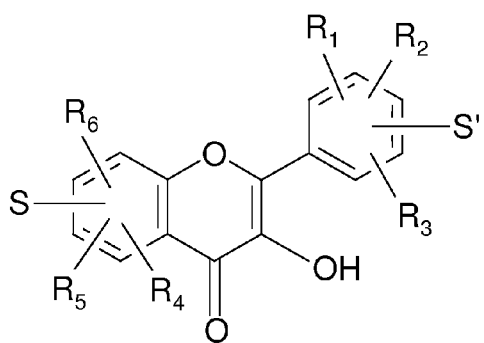
Figure 6:
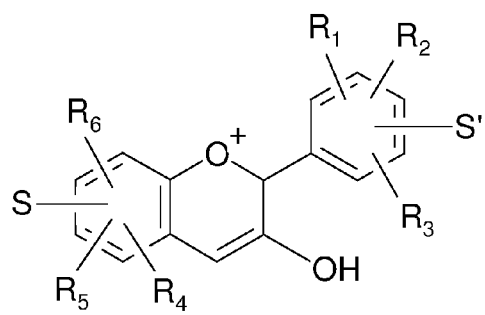

1D $^1$H, $^{13}$C NMR and 2D NMR experiments were run on a Bruker Avance AV-300 spectrometer at 300 MHz ($^1$H) and 75 MHz ($^{13}$C). The 2D experiments edited-HSQC, $^1$H-$^1$H COSY, NOESY, TOCSY, and HMBC were acquired using standard Bruker pulse sequences. Compound-580 was measured in Methanol-$d_4$. Each of these experiments required long runs to acquire sufficient signal intensity. For example, the $^{13}$C NMR experiment of Compound-580 took a protracted amount of time. FIGS. 4 and 5 show the 1D $^1$H-NMR and $^{13}$C NMR spectra of Compound-580.

LC-MS and NMR analyses of Compound-580 indicated that it was of very high purity. Therefore, excellent NMR spectra of this compound was obtained, despite the small amounts purified. High purity was also important for bioassay specificity.

The structural elucidation of the compound has been performed on the basis of spectroscopic methods. Extensive interpretation of 1D and 2D NMR spectra of this compound and comparison of its NMR data with those of literature data (Bucar, F.; Ninov, S.; Ionkova, I.; Kartnig, T.; Schubert-Zsilavecz, M.; Asenov, I.; Konuklugil, B.; Flavonoids from *Phlomis nissolii. Phytochemistry*, 1998, 48: 573-575.) resulted in the identification of Compound-580 as luteolin 7-(6"-β-D-apiofuranosyl)-β-D-glucopyranoside or alternatively: 7-[(6-O-D-apio-beta-D-furanosyl-beta-D-glucopyranosyl)oxy]-2-(3,4-dihydroxyphenyl)-5-hydroxy-4H-1-benzopyran-4-one; chemical formula: C26H28O15; molecular weight: 580.49; structure shown in FIGS. 7 (Formula X) and 8 (Formula $X_1$).

Bioassays of pure Compound-580 were performed according to the Analgesic Bioassay Protocol (Example 1) and are summarized in Table 7.

EXAMPLE 5

Inflammation Bioassay Protocol

A mouse air pouch assay was used to determine the therapeutic effectiveness of various extracts/compounds as anti-inflammatories in the present invention.

To induce air pouches, 10-15 week old mice were injected subcutaneously on the back with 3 ml of air.

On day 2, the pouches were reinflated with 1.5 m. of air.

On day 6, inflammation was induced by injecting 1 ml of a suspension of carrageenan (2% weight/volume in calcium-free and magnesium-free phosphate buffered saline (PBS) solution) into the air pouch.

100 μL of solution including test compounds were injected with the carrageenan (additional 100 μL of PBS were injected into the controls).

After 4 hours, the mice were sacrificed by including $CO_2$ narcosis, the pouches were flushed with 2 ml of PBS, and exudates were harvested.

Exudates were diluted 1:1 with 0.015% methylene blue in PBS.

White blood cells were counted in a standard hemocytometer chamber (American Optical, Buffalo, N.Y.).

EXAMPLE 6

Inflammation Bioassay Results

Compound 580 (Formulas X and Xi) was assayed for anti-inflammatory activity according to the Inflammation Bioassay Protocol (Example 5). With the carrageenan injection, five mice received injections of 100 μL of test solution containing Compound 580, and eleven control mice received injections of 100 μL of PBS. The exudates were harvested from the air pouches and white blood cells counted, the results of which are set forth in Table 8 (Control) and Table 9 (Compound 660).

TABLE 7

Analgesic Bioassay Results: Pure Compound-580 (Formula X)

| Fraction/Pure | n | Avg Baseline | Avg Cap 20 | Avg Cap 25 | Avg Cap 30 | Avg All Cap | Avg Ext 5 | Avg Ext 20 | Avg Ext 30 |
|---|---|---|---|---|---|---|---|---|---|
| Frac i2 580 (0.08 mg) | 5 | 13.97667 | 7.33 | 7.03 | 6.56 | 6.973333 | 19.42 | 11.9 | 8.7 |
| SEM | | 0.719673 | 1.316038 | 0.250355 | 0.30485 | 0.316879 | 0.432512 | 1.726332 | 1.423376 |
| Control | 5 | 12.60667 | 11.42 | 12.03 | 11.43 | 11.62667 | 13.21 | 12.05 | 12.68 |
| SEM | | 0.719673 | 1.316038 | 1.279935 | 0.72081 | 0.636548 | 1.126198 | 1.171443 | 0.83264 |
| Pure 580 "C-5"(0.23 mg) | 5 | 9.3 | 5.8 | 7.2 | 6 | 6.3 | 13.7 | 9.6 | 9.4 |
| SEM | | 0.3399 | 0.630212 | 0.822226 | 0.6177378 | 0.4044788 | 1.265476 | 1.42969 | 1.414375 |
| Control | 5 | 10 | 8.2 | 11.6 | 10.4 | 10.1 | 11.6 | 11.8 | 9.6 |
| SEM | | 0.5781 | 0.890513 | 1.5715153 | 2.0996436 | 0.9096487 | 1.136412 | 1.575027 | 0.960937 |
| Frac iB 746 (0.13 mg) | 5 | 10.63333 | 9.47 | 7.84 | 7.32 | 8.21 | 12.22 | 6.79 | 7.98 |
| SEM | | 0.738914 | 1.441762 | 0.844748 | 0.570341 | 0.592818 | 1.678346 | 0.860032 | 0.810871 |
| Control | 5 | 12.75 | 12.63 | 12.14 | 13.81 | 12.86 | 12.07 | 13.04 | 12.76 |
| SEM | | 0.738914 | 1.056625 | 1.171912 | 1.319802 | 0.674317 | 1.151719 | 1.278384 | 1.267473 |

Latencies after application of the fraction i2 at 20 minutes as compared to the 30 minute capsaicin latencies were statistically significant (by single factor ANOVA) with a of P-value of 0.00695081.

Latencies after application of the pure Compound-580 at 20 minutes as compared to the minute capsaicin latencies were statistically significant (by single factor ANOVA) with a of P-value of 0.02443097.

TABLE 8

Inflammation Bioassay Results: Controls

| Mouse Number | Volume (ml) | Cell Count (4 chambers) | | | | Average Count | Dilution Factor | Cells/ml | Cells ($10^6$/ml) | Average Cells ($10^6$/ml) |
|---|---|---|---|---|---|---|---|---|---|---|
| 1  | 2   | 98  | 103 | 145 | 86  | 108.00 | 216     | 2.16E+06 | 2.16 | 2.67 |
| 2  | 2   | 80  | 93  | 100 | 78  | 87.75  | 175.5   | 1.76E+06 | 1.76 |      |
| 3  | 2   | 68  | 84  | 78  | 110 | 85.00  | 170     | 1.70E+06 | 1.70 |      |
| 4  | 2   | 56  | 100 | 72  | 95  | 80.75  | 161.5   | 1.62E+06 | 1.62 |      |
| 5  | 2   | 167 | 65  | 74  | 111 | 104.25 | 208.5   | 2.09E+06 | 2.09 |      |
| 9  | 3   | 82  | 98  | 79  | 104 | 90.75  | 272.25  | 2.72E+06 | 2.72 |      |
| 10 | 3   | 63  | 95  | 86  | 119 | 90.75  | 272.25  | 2.72E+06 | 2.72 |      |
| 14 | 3.5 | 150 | 108 | 48  | 67  | 93.25  | 326.375 | 3.26E+06 | 3.26 |      |
| 15 | 3.5 | 75  | 120 | 132 | 128 | 113.75 | 398.125 | 3.98E+06 | 3.98 |      |
| 16 | 2.5 | 259 | 156 | 125 | 234 | 193.0  | 483.75  | 4.84E+06 | 4.84 |      |
| 17 | 2   | 130 | 86  | 95  | 199 | 127.50 | 255     | 2.55E+06 | 2.55 |      |

TABLE 9

Inflammation Bioassay Results: Compound 580

| Mouse Number | Volume (ml) | Cell Count (4 chambers) | | | | Average Count | Dilution Factor | Cells/ml | Cells ($10^6$/ml) | Average Cells ($10^6$/ml) | P-value |
|---|---|---|---|---|---|---|---|---|---|---|---|
| 6  | 3 | 25 | 19 | 24 | 28 | 24.00 | 72     | 7.20E+05 | 0.72 | 1.00 | 0.00306516 |
| 7  | 3 | 40 | 43 | 59 | 13 | 38.75 | 116.25 | 1.16E+06 | 1.16 |      |            |
| 8  | 3 | 56 | 30 | 16 | 60 | 40.50 | 121.5  | 1.22E+06 | 1.22 |      |            |
| 18 | 2 | 26 | 49 | 33 | 42 | 37.50 | 75     | 7.50E+05 | 0.75 |      |            |
| 19 | 2 | 58 | 62 | 67 | 47 | 58.50 | 117    | 1.17E+06 | 1.17 |      |            |

As shown, the average white cell volume ($10^6$ cells per ml) in aliquots from mice treated with test Compound 580 is 1.00 compared to 2.67 in the control mice, establishing the efficacy of Compound 580 as an anti-inflammatory (P-value of 0.00306516). The anti-inflammatory effects of Compound 580 are comparable to 0.5-1.0 mg/kg/week of chronic methotrexate, or 1.5 mg/kg acute dose of dexamethasone.

EXAMPLE 7

Identification of Therapeutic Flavonoid Glycosides and Combinations

Using the teachings provided herein, one of skill in the art will be able to determine flavonoid glycosides exhibiting therapeutic activity and suitable for use in the present invention, for example and without limitation, by bioassaying various flavonoid glycosides according to Formulas IV, XIII, XIX, XXVII, XXXIII, and XXXVII according to the protocol set forth in the Analgesic Bioassay of Example 1. Further, conventional animal models may be used to determine the therapeutic utility of various flavonoid glycosides, and therefore their suitability for use in the present invention.

Moreover, as discussed herein, compounds of the present invention may be combined with known therapeutic agents, such as analgesics, in pharmaceutical compositions. Such analgesics include, but are not limited to, NSAIDS such as salicylates, acetaminophen, ibuprofen and COX-2 inhibitors. Using the Analgesic Bioassay of Example 1 and conventional animal models, one of skill in the art will be able to determine the effectiveness of such combinations as analgesics, and accordingly such combinations are also within the scope of the present invention.

Stereochemistry

As will be readily appreciated by one of skill in the art, all stereoisomers of compounds exhibiting therapeutic activity are suitable for use in the present invention, and are therefore within the scope of the present invention. As discussed herein, for example and without limitation, enantiomers, diastereomers, racemic mixtures, and enantiomerically-enriched mixtures, of such compounds are within the scope of the present invention.

The invention has been described herein above with reference to various and specific embodiments and techniques. It will be understood, however, that reasonable modifications of such embodiments and techniques can be made without substantially departing from either the spirit or scope of the invention defined by the following claims. All references cited herein are incorporated in their entirety.

What is claimed is:

1. A pharmaceutical composition comprising a therapeutically effective amount of a compound of Formula X

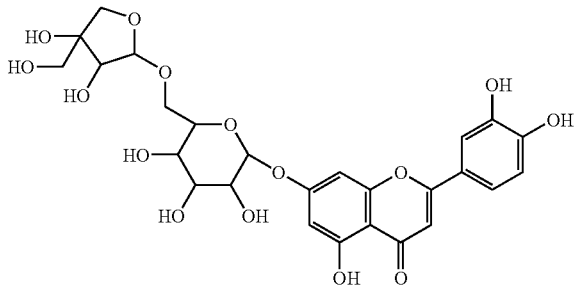

or Formula Xi

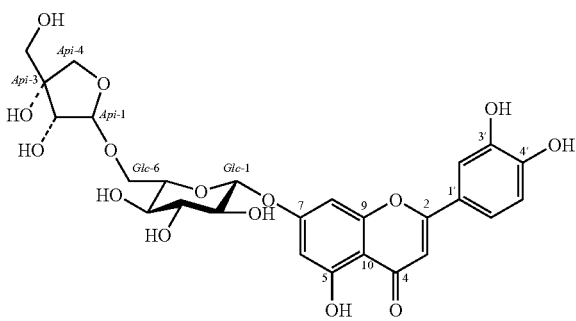

or a pharmaceutically-acceptable salt, enantiomer, diasteriomer, racemic mixture, enantomerically-enriched mixture, solvate, or prodrug thereof, in a pharmaceutically effective carrier.

2. A pharmaceutical composition according to claim 1, wherein said compound is present in an amount that is therapeutically effective to effect analgesia or reduce inflammation in a mammal.

3. A pharmaceutical composition according to claim 1, wherein said composition is in a form selected from the group consisting of: an immediate-release composition, a controlled-release composition, sustained-release orally-administrable compositions, topically-administrable compositions, liquid solutions, liquid sprays, lozenges, throat sprays, ointments, solutions, foams, cough drops, dissolvable strips, a jelly, a mouthwash; a gargle, a lollipop, a gum, aqueous or oily suspensions, dispersible powders or granules, a syrup, an elixir, emulsions, a cream, a paste, a gel, a lotion, impregnated dressings, occularly-administrable compositions, inhalable particles, inhalable solutions, droplets, and aerosols.

4. A pharmaceutical composition according to claim 1, wherein said compound according to Formula X or Xi is produced synthetically, semi-synthetically, or is isolated and purified from a naturally occurring organism.

5. A pharmaceutical composition according to claim 1, further comprising one or more therapeutic agents in combination with said compound according to Formula X or Xi, said therapeutic agents being selected from the group consisting of analgesics, anti-inflammatories, NSAIDs, salicylates, acetaminophen, ibuprofen, and COX-2 inhibitors.

6. A pharmaceutical composition according to claim 2, wherein said amount that is therapeutically effective to effect analgesia or reduce inflammation in a mammal is between about 0.01 mg to 500 mg per unit dose.

7. A method for effecting analgesia or reducing inflammation in a mammal, comprising administering to a mammal a pharmaceutical composition comprising a therapeutically effective amount of a compound of Formula X

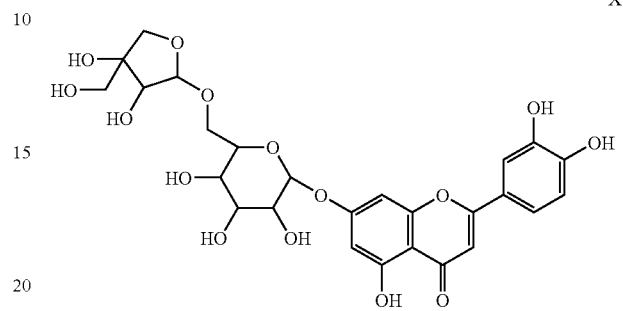

or Formula Xi

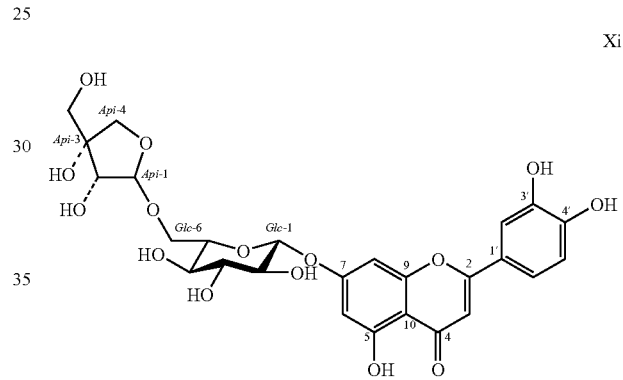

or a pharmaceutically-acceptable salt, enantiomer, diasteriomer, racemic mixture, enantomerically-enriched mixture, solvate, or prodrug thereof, in a pharmaceutically effective carrier.

8. A method for providing therapeutic treatment to a mammal according to claim 7, wherein said therapeutic treatment is for a condition selected from the group consisting of:

fever; rheumatic fever; symptoms associated with influenza or other viral infections; common cold; low back and neck pain; dysmenorrhea; headache; toothache; sprains and strains; myositis;

neuralgia; synovitis; arthritis, rheumatoid arthritis; degenerative joint diseases, including osteoarthritis; gout; ankylosing spondylitis; bursitis; burns; injuries; and pain and inflammation following surgical and dental procedures.

9. A method for providing therapeutic treatment to a mammal according to claim 7, wherein said pharmaceutical composition is provided in a form selected from the group consisting of: an immediate-release composition, a controlled-release composition, sustained- release orally-administrable compositions, topically-administrable compositions, liquid solutions, liquid sprays, lozenges, throat sprays, ointments, solutions, foams, cough drops, dissolvable strips, a jelly, a mouthwash; a gargle, a lollipop, a gum, aqueous or oily suspensions, dispersible powders or granules, a syrup, an elixir, emulsions, a cream, a paste, a gel, a lotion, impregnated dressings, occularly-administrable compositions, inhalable particles, inhalable solutions, droplets, and aerosols.

10. A method for providing therapeutic treatment to a mammal according to claim 7, wherein said pharmaceutical composition further comprises one or more therapeutically-active agents in combination with said compound according to Formula Va, said therapeutic agents being selected from the group consisting of analgesics, anti-inflammatories, NSAIDs, salicylates, acetaminophen, ibuprofen, and COX-2 inhibitors.

11. A method for providing therapeutic treatment to a mammal according to claim 7, wherein said pharmaceutical composition is administered to said mammal between about 0.01 mg to 500 mg per unit dose.

* * * * *